United States Patent
McCracken, Jr. et al.

(10) Patent No.: US 11,817,207 B1
(45) Date of Patent: Nov. 14, 2023

(54) MEDICATION INVENTORY SYSTEM INCLUDING IMAGE BASED BOUNDARY DETERMINATION FOR GENERATING A MEDICATION TRAY STOCKING LIST AND RELATED METHODS

(71) Applicant: Inmar Rx Solutions, Inc., Ft. Worth, TX (US)

(72) Inventors: James W. McCracken, Jr., Lewisville, NC (US); Gregory J. Brendel, West Mifflin, PA (US); Patrick S. Connelly, Carnegie, PA (US); Marko Milojevic, Jamestown, NC (US); Jared O. Santibanez, Forney, TX (US); Juleo Amosah, Winston-Salem, NC (US); Justin A. Krull, Weirton, WV (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 0 days.

(21) Appl. No.: 17/528,797

(22) Filed: Nov. 17, 2021

Related U.S. Application Data

(63) Continuation-in-part of application No. 17/217,991, filed on Mar. 30, 2021, which is a
(Continued)

(51) Int. Cl.
  *A61J 7/00* (2006.01)
  *G06T 7/13* (2017.01)
  (Continued)

(52) U.S. Cl.
  CPC ............ *G16H 40/20* (2018.01); *A61J 7/0069* (2013.01); *G06T 7/13* (2017.01); *G16H 30/00* (2018.01);
  (Continued)

(58) Field of Classification Search
  CPC ........ G06V 20/52; G06V 10/25; G06V 10/56; G06V 10/44; G06V 10/10; G06V 40/161;
  (Continued)

(56) References Cited

U.S. PATENT DOCUMENTS 3,069,654 A 12/1962 Hough
4,768,661 A 9/1988 Pfeifer
(Continued)

FOREIGN PATENT DOCUMENTS

| EP | 1089229 | 4/2001 | |
|---|---|---|---|
| EP | 1207683 A2 * | 5/2002 | ............ G06T 11/60 |
| WO | 2017220868 | 12/2017 | |

OTHER PUBLICATIONS

Fiala, "ARTag, a fiducial marker system using digital techniques" (Year: 2005).*
(Continued)

*Primary Examiner* — Thien T Mai
(74) *Attorney, Agent, or Firm* — ALLEN, DYER, DOPPELT, + GILCHRIST, P.A.

(57) ABSTRACT

A medication tray may include a boundary wall defining a boundary outline. Markers may be carried by the boundary wall. A mobile device may obtain a first image of the medication tray, and determine a number of the markers from the first image. When the number equals or exceeds a threshold, an edge detection algorithm may be applied to the first image to identify the boundary outline based upon the markers, and generate a stocking list of the tray based upon the outline. When the determined number does not exceed the threshold, the device may obtain a second image of the tray, and determine an updated number of the markers from the first and second images. When the updated number equals or exceeds the threshold, the algorithm may be applied to the images to identify the outline based upon the
(Continued)

markers, and generate the stocking list based upon the outline.

26 Claims, 34 Drawing Sheets

Related U.S. Application Data continuation-in-part of application No. 16/793,098, filed on Feb. 18, 2020, which is a continuation-in-part of application No. 16/704,573, filed on Dec. 5, 2019, now Pat. No. 11,462,312.

(51) Int. Cl.
*G16H 40/20* (2018.01)
*G16H 30/00* (2018.01)
*G16H 40/67* (2018.01)

(52) U.S. Cl.
CPC ... *G16H 40/67* (2018.01); *G06T 2207/10024* (2013.01)

(58) Field of Classification Search
CPC ....... G06V 10/225; G06T 7/0012; G06T 7/11; G06T 2207/30204; A61J 7/0069; A61J 1/035; A61J 1/16; A61J 2205/10; A61J 2205/20
See application file for complete search history.

(56) References Cited

U.S. PATENT DOCUMENTS

| | | | |
|---|---|---|---|
| 6,332,285 B1 | 12/2001 | Aaldenberg et al. |
| 7,085,432 B2 | 8/2006 | Paquette |
| 7,599,516 B2 | 10/2009 | Limer et al. |
| 8,861,816 B2 | 10/2014 | Lang et al. |
| 8,966,863 B2 | 3/2015 | Amano et al. |
| 9,757,305 B2 | 9/2017 | Ika et al. |
| 9,910,965 B2 | 3/2018 | Bufalini et al. |
| 10,083,366 B2 | 9/2018 | Song et al. |
| 10,357,428 B2 | 7/2019 | Ika et al. |
| 11,030,752 B1 | 6/2021 | Backlund et al. |
| 2007/0239482 A1 | 10/2007 | Finn et al. |
| 2010/0027845 A1* | 2/2010 | Kim ........................ G06F 18/29 |
| | | | 382/107 |
| 2012/0069383 A1 | 3/2012 | Hines et al. |
| 2012/0319550 A1* | 12/2012 | Manniso ............... A47B 88/994 |
| | | | 312/348.3 |
| 2013/0070090 A1 | 3/2013 | Bufalini et al. |
| 2013/0091679 A1 | 4/2013 | Gloger et al. |
| 2014/0042229 A1* | 2/2014 | Tsai ..................... G06K 7/1417 |
| | | | 235/462.11 |
| 2014/0214438 A1 | 7/2014 | Ahmadi |
| 2014/0288952 A1 | 9/2014 | Smith et al. |
| 2016/0147976 A1 | 5/2016 | Jain et al. |
| 2016/0364686 A1* | 12/2016 | Wolfe ................ G06K 7/10861 |
| 2017/0098049 A1 | 4/2017 | Sweeney |
| 2017/0246083 A1 | 8/2017 | Amano et al. |
| 2017/0270508 A1 | 9/2017 | Roach et al. |
| 2018/0260665 A1 | 9/2018 | Zhang et al. |
| 2019/0333008 A1 | 10/2019 | Wolfe et al. |
| 2020/0296062 A1 | 9/2020 | Wilson |
| 2021/0298994 A1 | 9/2021 | Liu et al. |
| 2022/0008291 A1 | 1/2022 | Grosfils et al. |

OTHER PUBLICATIONS

Mccracken, Jr. et al., U.S. Appl. No. 16/395,343, filed Apr. 26, 2019.
Mccracken, Jr. et al., U.S. Appl. No. 16/395,353, filed Apr. 26, 2019.
Rogers et al., U.S. Appl. No. 16/704,573, filed Dec. 5, 2019.
Rogers et al., U.S. Appl. No. 16/793,098, filed Feb. 18, 2020.
Rogers et al., U.S. Appl. No. 17/162,781, filed Jan. 29, 2021.
Rogers et al., U.S. Appl. No. 17/217,991, filed Mar. 30, 2021.
Duda et al., "Use of the Hough Transformation to Detect Lines and Curves in Pictures", Graphics and Image Processing, Communications of the ACM, vol. 15, No. 1, Jan. 1972, pp. 11-15.
Peter Hart, "How the Hough Transform Was Invented", IEEE Signal Processing Magazine, Nov. 2009, pp. 1-5.

* cited by examiner

MEDICATION INVENTORY SYSTEM INCLUDING IMAGE BASED BOUNDARY DETERMINATION FOR GENERATING A MEDICATION TRAY STOCKING LIST AND RELATED METHODS

RELATED APPLICATIONS

The present application is a continuation-in-part of U.S. patent application Ser. No. 17/217,991 filed Mar. 30, 2021, which is a continuation-in-part of U.S. patent application Ser. No. 16/793,098, filed Feb. 18, 2020, which is a continuation-in-part of U.S. patent application Ser. No. 16/704,573, filed Dec. 5, 2019, the entire contents of all of which are hereby incorporated by reference.

TECHNICAL FIELD

The present invention relates to the field of medicine, and, more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/0260665 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication inventory system may include a medication tray including a plurality of compartments for storing respective medications. The medication tray may include a boundary wall defining a boundary outline of the medication tray, and the medication tray may have a tray identifier associated therewith. The medication inventory system may also include a plurality of boundary markers carried by the boundary wall, and a mobile wireless communications device configured to obtain a first image of the medication tray, and determine a number of the plurality of boundary markers from the first image. The mobile wireless communications device may be configured to, when the determined number equals or exceeds a threshold number, apply an edge detection algorithm to the first image to identify the boundary outline of the medication tray based upon the plurality of boundary markers, and generate a current medication stocking list of the medication tray based upon the identified boundary outline and the tray identifier from the first image. When the determined number does not exceed the threshold number, the mobile wireless communications device may be configured to obtain at least one second image of the medication tray, and determine an updated number of the plurality of boundary markers from the first and the at least one second images. When the updated determined number equals or exceeds the threshold number, the mobile wireless communications device may be configured to apply the edge detection algorithm to the first and at least one second images to identify the boundary outline of the medication tray based upon the plurality of boundary markers, and generate the current medication stocking list of the medication tray based upon the identified boundary outline and the tray identifier from the first and at least one second images.

The mobile wireless communication device may be configured to, when the determined number does not exceed the threshold number, determine whether the at least one second image is a same image of the first image based upon pixel distances, and when so, discard the at least one second image. The first and at least one second images each may include respective first and at least one second pixel sets, and the mobile wireless communications device may be configured to determine whether the at least one second image is the same as the first image based upon alignment of the first and at least one second pixel sets.

Each boundary marker may include a body having a slot therein to be slidably positioned on the boundary wall. Each boundary marker may have machine readable indicia on an upper surface thereof, for example. Each boundary marker may have a color different than the boundary wall.

The mobile wireless communications device may be configured to extract red, green, blue (RGB) pixel data from the at least one image, and convert the RGB pixel data to hue saturation value (HSV) space, for example. The mobile wireless communications device may also be configured to segment the at least one image into colored segments based upon the HSV space, and apply the edge detection algorithm to the colored segments to identify the boundary outline of the medication tray.

The mobile wireless communications device may be configured to apply contour tracing to identify the boundary outline of the medication tray, for example. The mobile wireless communications device may be configured to identify corners of the boundary outline of the medication tray based upon the edge detection algorithm.

The mobile wireless communications device may be configured to determine a desired medication stocking list for the medication tray based upon the tray identifier, for example. The mobile wireless communications device may be configured to determine at least one missing medication based upon the current medication stocking list and the desired medication stocking list, for example.

A method aspect is directed to a method of processing medication inventory in a medication inventory system that includes a medication tray that includes a plurality of compartments for storing respective medications. The medication tray also includes a boundary wall defining a boundary outline of the medication tray, and the medication tray may have a tray identifier associated therewith. The method may include using a mobile wireless communications device to obtain a first image of the medication tray, and determine a number of the plurality of boundary markers from the first image. When the determined number equals or exceeds a threshold number, the method may include using the mobile wireless communications device to apply an edge detection algorithm to the first image to identify the boundary outline of the medication tray based upon a plurality of boundary markers, and generate a current medication stocking list of the medication tray based upon the identified boundary outline and the tray identifier from the first image. The method may also include using the mobile wireless communications device to, when the determined number does not exceed the threshold number, obtain at least one second image of the medication tray, and determine an updated number of the plurality of boundary markers from the first and at least one second image. When the updated determined number equals or exceeds the threshold number, the method may include using the mobile wireless communications device to apply the edge detection algorithm to the first and at least one second images to identify the boundary outline of the medication tray based upon the plurality of boundary markers, and generate the current medication stocking list of the medication tray based upon the identified boundary outline and the tray identifier from the first and at least one second images.

A computer readable medium aspect is directed to a non-transitory computer readable medium for a medication inventory system that includes a medication tray including a plurality of compartments for storing respective medications. The medication tray includes a boundary wall defining a boundary outline of the medication tray, and the medication tray has a tray identifier associated therewith. The non-transitory computer readable medium includes computer executable instructions that when executed by a controller of a mobile wireless communications device cause the controller to perform operations. The operations may include obtaining a first image of the medication tray, and determining a number of the plurality of boundary markers from the first image. The operations may also include, when the determined number equals or exceeds a threshold number, applying an edge detection algorithm to the first image to identify the boundary outline of the medication tray based upon the plurality of boundary markers, and generating a current medication stocking list of the medication tray based upon the identified boundary outline and the tray identifier from the first image. The operations may also include, when the determined number does not exceed the threshold number, obtaining at least one second image of the medication tray, and determining an updated number of the plurality of boundary markers from the first and the at least one second images. The operations may further include, when the updated determined number equals or exceeds the threshold number, applying the edge detection algorithm to the first and at least one second images to identify the boundary outline of the medication tray based upon the plurality of boundary markers, and generating the current medication stocking list of the medication tray based upon the identified boundary outline and the tray identifier from the first and at least one second images.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation are used to indicate similar elements in alternative embodiments.

Figure 1:
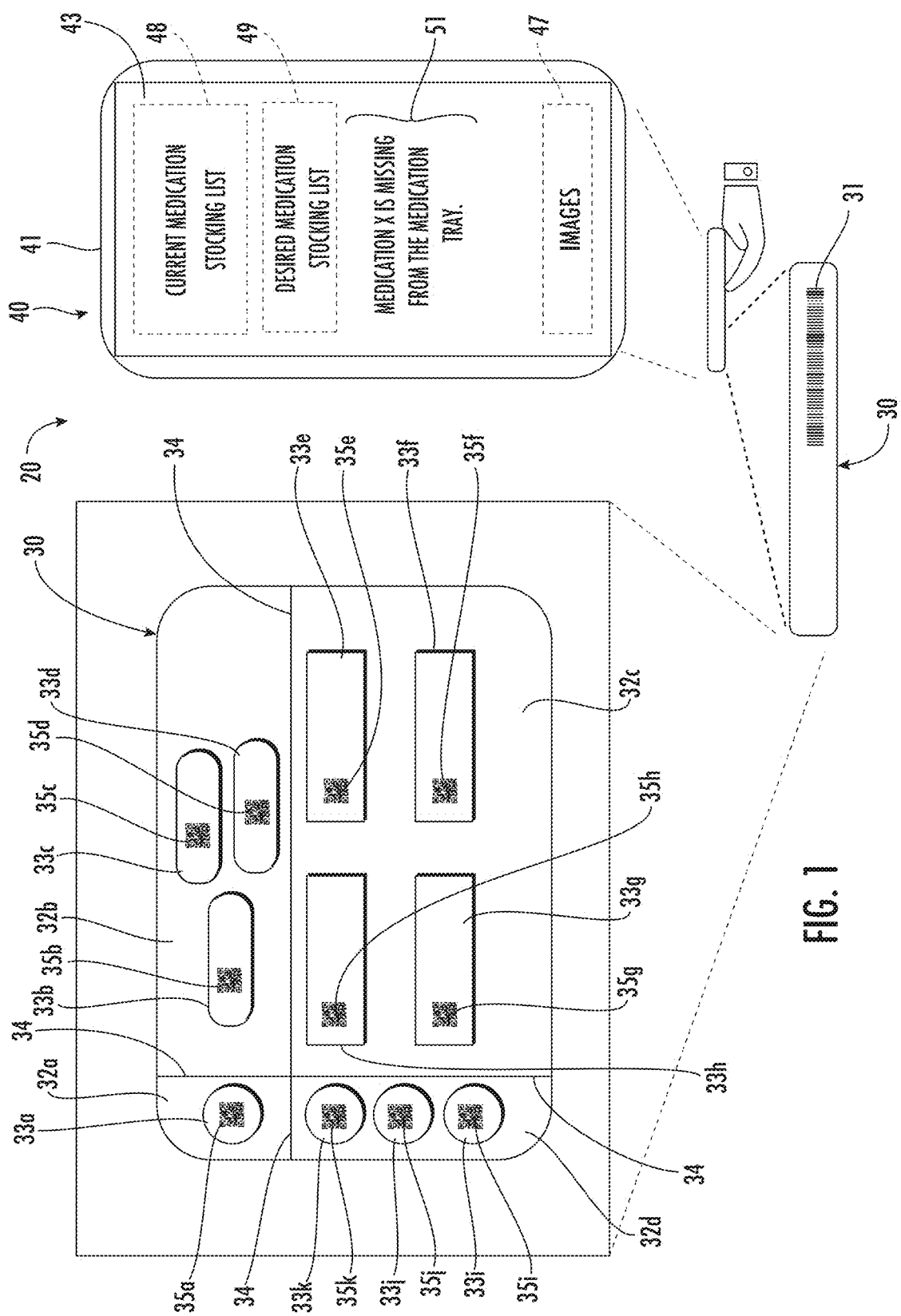
FIG. 1 is a schematic diagram of a medication inventory system in accordance with an embodiment.
Figure 2:
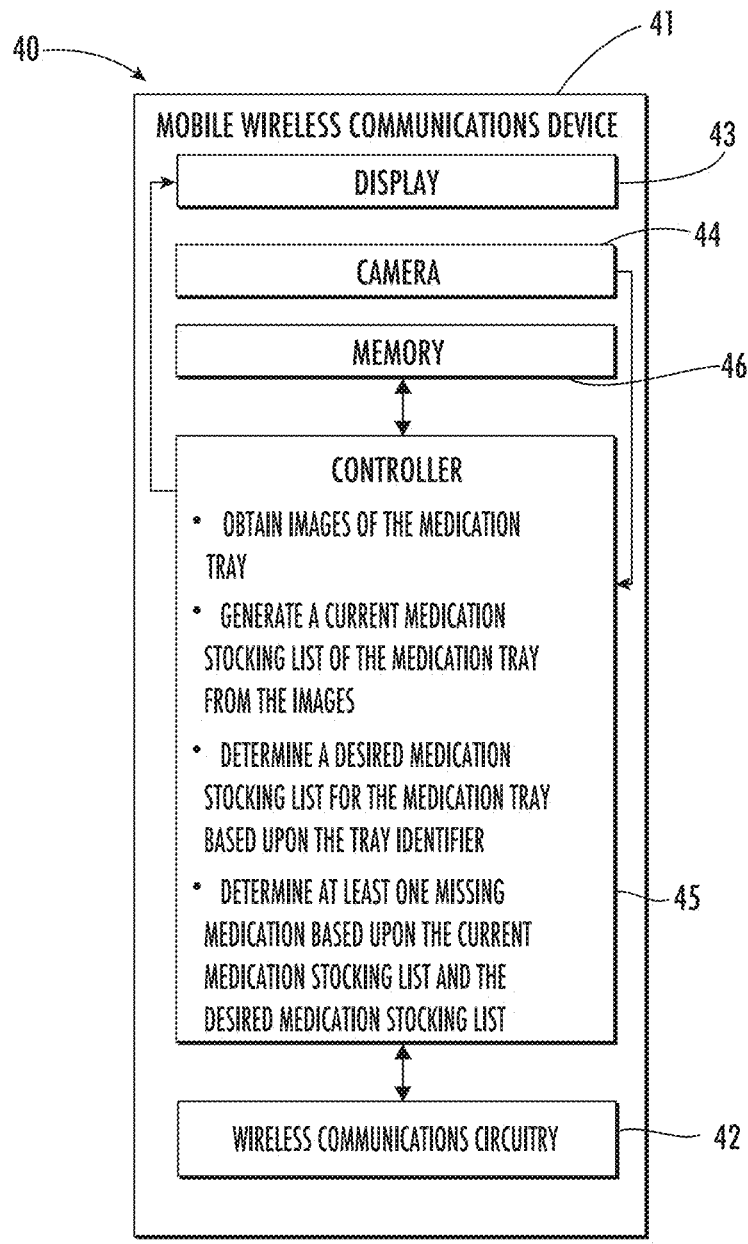
FIG. 2 is a schematic block diagram of the medication inventory system of FIG. 1.

Referring initially to FIGS. 1 and 2, a medication inventory system 20 illustratively includes a medication tray 30. The medication tray 30 includes partitions 34 that define compartments 32a-32n. Each compartment may store a medication 33a-33n, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc. For example, the medication tray 30 may be in the form of a drawer within a medication cabinet or medication dispensing cabinet. Each medication 33a-33n has a respective medication identifier 35a-35n associated therewith, for example, a barcode, quick-response (QR) code, alphanumeric characters, or other optically recognizable and unique code.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, QR code, alphanumeric characters, or other optically recognizable and unique code.

The medication inventory system 20 also includes a mobile wireless communications device 40, illustratively in the form of a smartphone. The mobile wireless communications device 40 illustratively includes a housing 41 and wireless communications circuitry 42 carried by the housing. The mobile wireless communications device 40 also includes a display 43, for example, a touch display, carried by the housing 41. A controller 45 is coupled to the wireless communications circuitry 42 and the display 43. A camera 44 is also carried by the housing 41 and coupled to the controller 45. One or more input devices may be carried by the housing 41 and coupled to the controller 45. While the mobile wireless communications device 40 is illustratively in the form of a smartphone, the mobile wireless communications device may be in the form of a tablet, laptop computer, or wearable device, for example.

Figure 3:
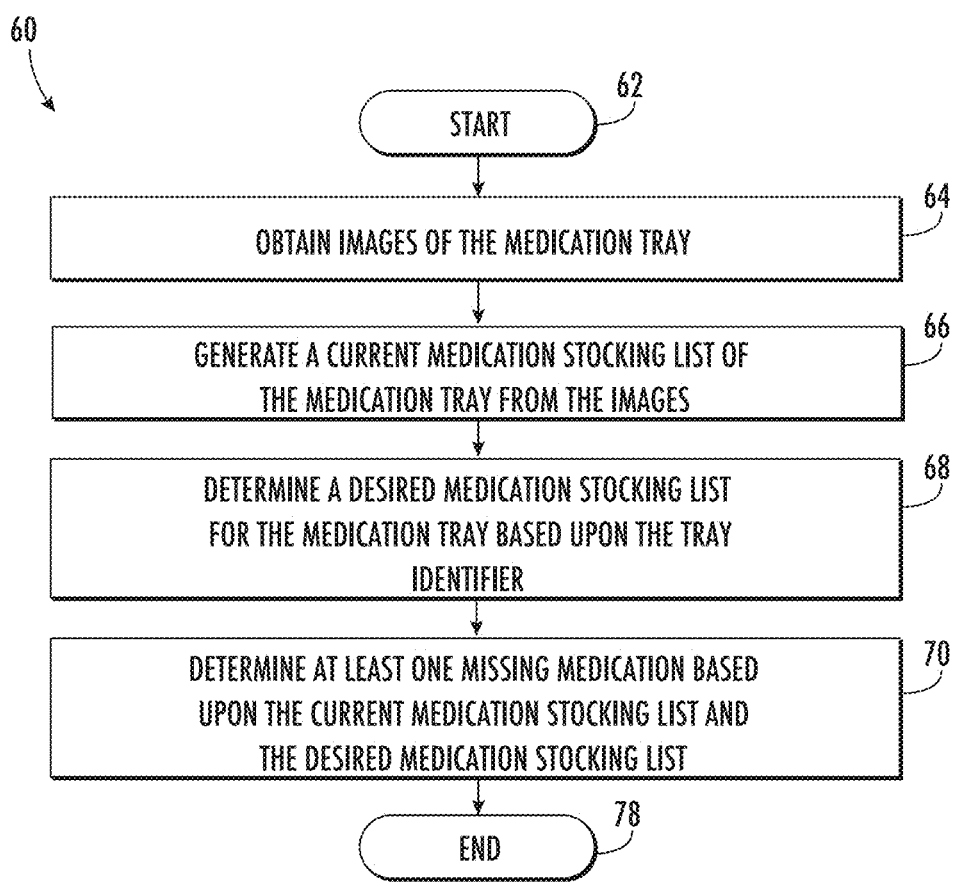
FIG. 3 is a flow diagram illustrating operation of the mobile wireless communications device of FIG. 2.
Figure 4:
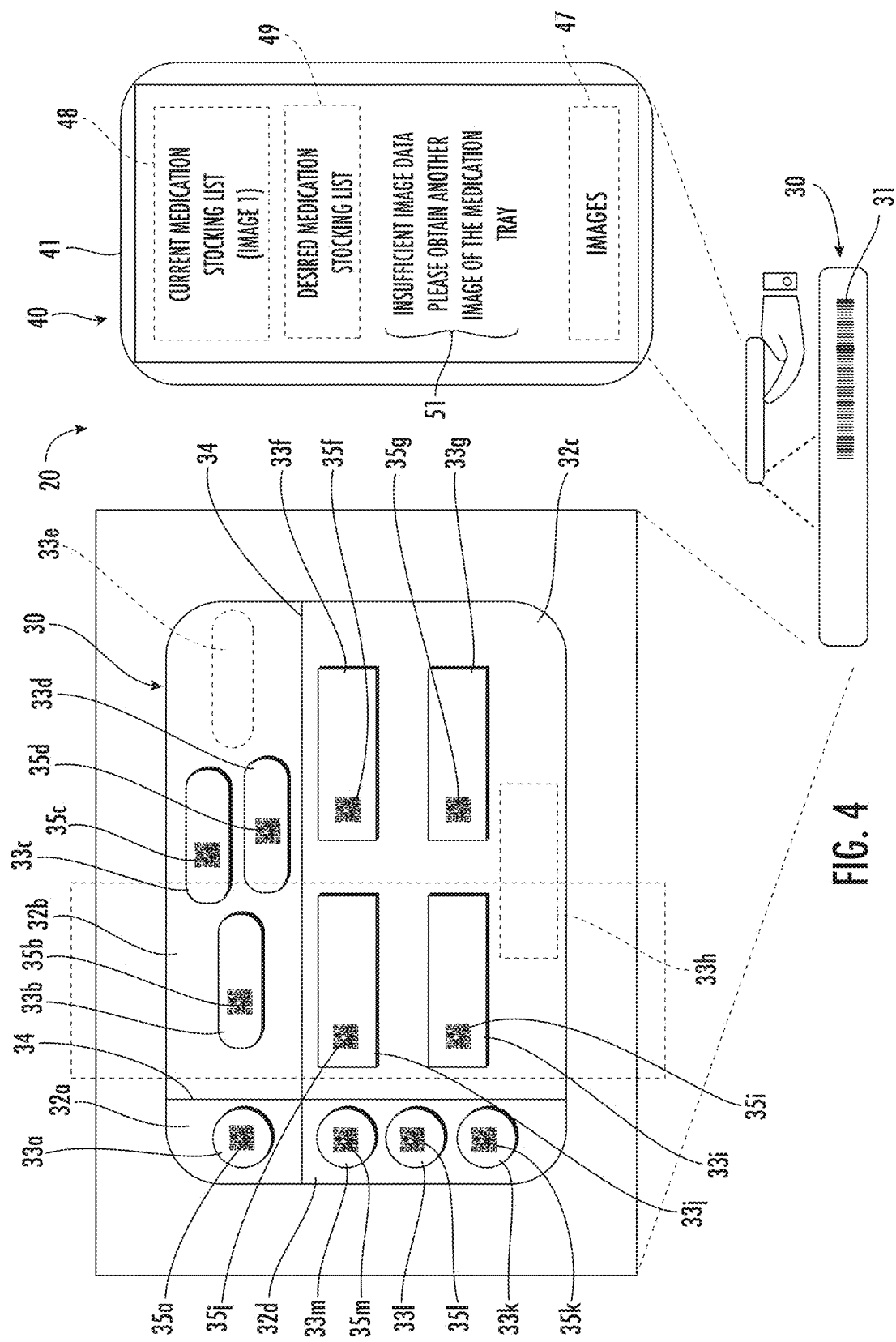
FIG. 4 is a schematic diagram of a medication inventory system in accordance with an embodiment.

Referring now additionally to the flowchart 60 in FIG. 3, beginning at Block 62, operations of the mobile wireless communications device 40 of the medication inventory system 20 will now be described. While operations of the mobile wireless communications device 40 are described, it will be appreciated by those skilled in the art that the controller 45 and an associated memory 46 cooperate to perform the operations.

At Block 64, the mobile wireless communications device 40 obtains images 47 of the medication tray 30. At Block 66, the mobile wireless communications device 40 generates a current medication stocking list 48 of the medication tray from the images 47.

The mobile wireless communications device 40 determines a desired medication stocking list 49 of the medication tray 30 based upon the tray identifier 31 (Block 68). More particularly, the mobile wireless communications device 40 may obtain the desired medication stocking list 49 from a remote computer or database based upon the tray identifier 31. In other words, the tray identifier 31 may be used as an index to retrieve or obtain the desired medication stocking list 49.

The mobile wireless communications device 40, at Block 70, determines one or more missing medications 33a-33n based upon the current medication stocking list 48 and the desired medication stocking list 49. More particularly, if a medication 33a-33n that is part of the desired medication stocking list 49 is determined to not be in the current medication stocking list 48 (i.e., a medication was not found in the images 47), a notification 51 may be generated and displayed on the display 43 of the mobile wireless communications device 40. The controller 45 may use image recognition techniques, for example, for identifying the medication identifiers 35a-35n, to determine missing medications. Operations end at Block 78.

Figure 8:
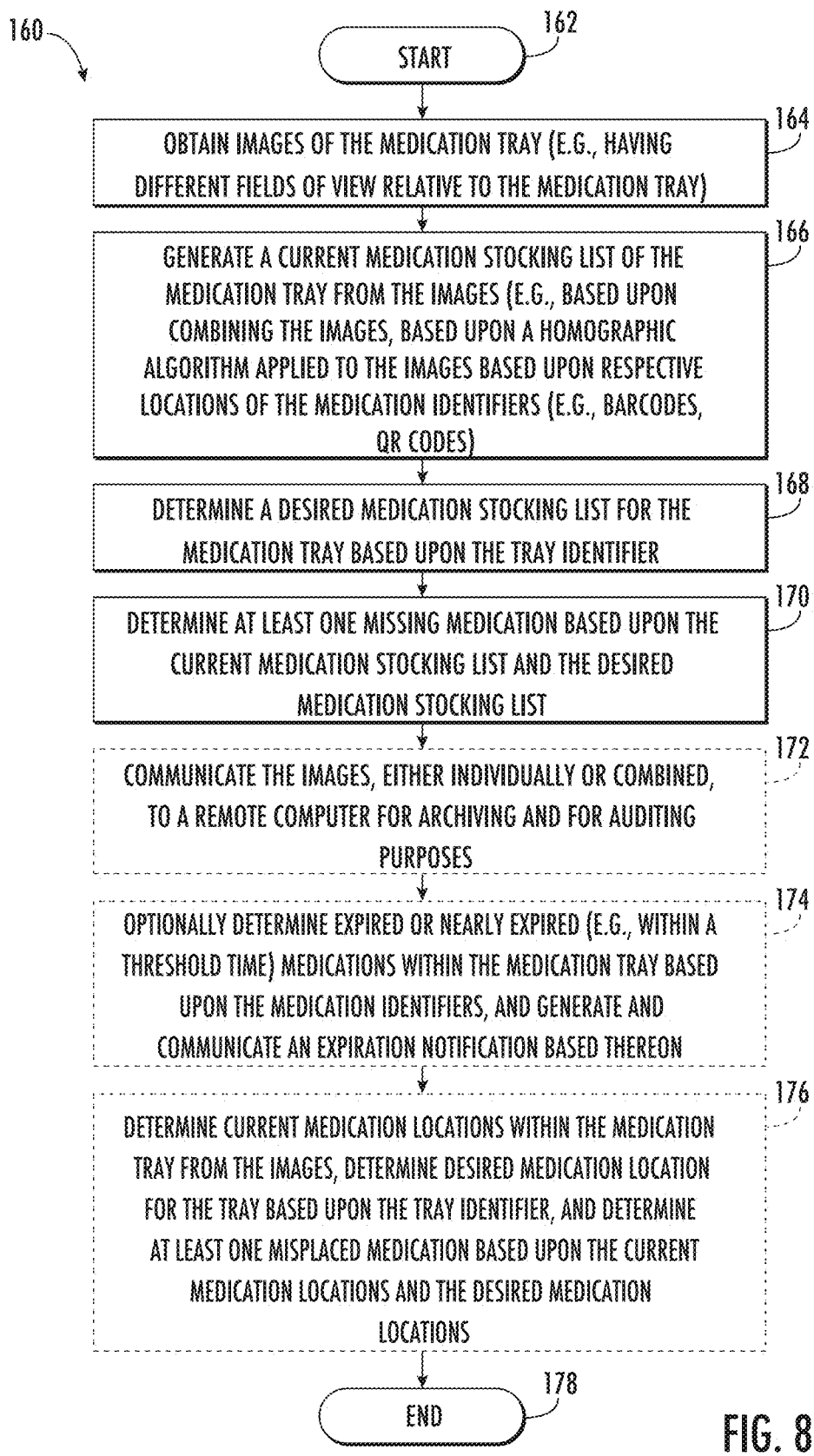
FIG. 8 is a flow diagram illustrating operation of the mobile wireless communications device of FIG. 4.

Referring now to FIGS. 4-7, and the flowchart 160 in FIG. 8, beginning at Block 162 more detailed operations of the mobile wireless communications device 40 with respect to the medication inventory system 20 will now be described. At Block 164, the mobile wireless communications device 40 obtains images 47 of the medication tray 30. The images 47 may include images having different fields of view relative to the medication tray 30. In other words, a given user may capture, via the camera 44, images of the medication tray 30. The images 47 may partially capture the medication tray 30. As will be appreciated by those skilled in the art, to obtain a high enough resolution to read both the tray and medication identifiers 31, 35, it may be desirable to position the mobile wireless communications device 40 including the camera 44 relatively close to the medication tray 30. As a result, a given image 47 may include only a portion of the medication tray 30 and thus not all medications 33a-33n would be in the field of view.

Figure 5:
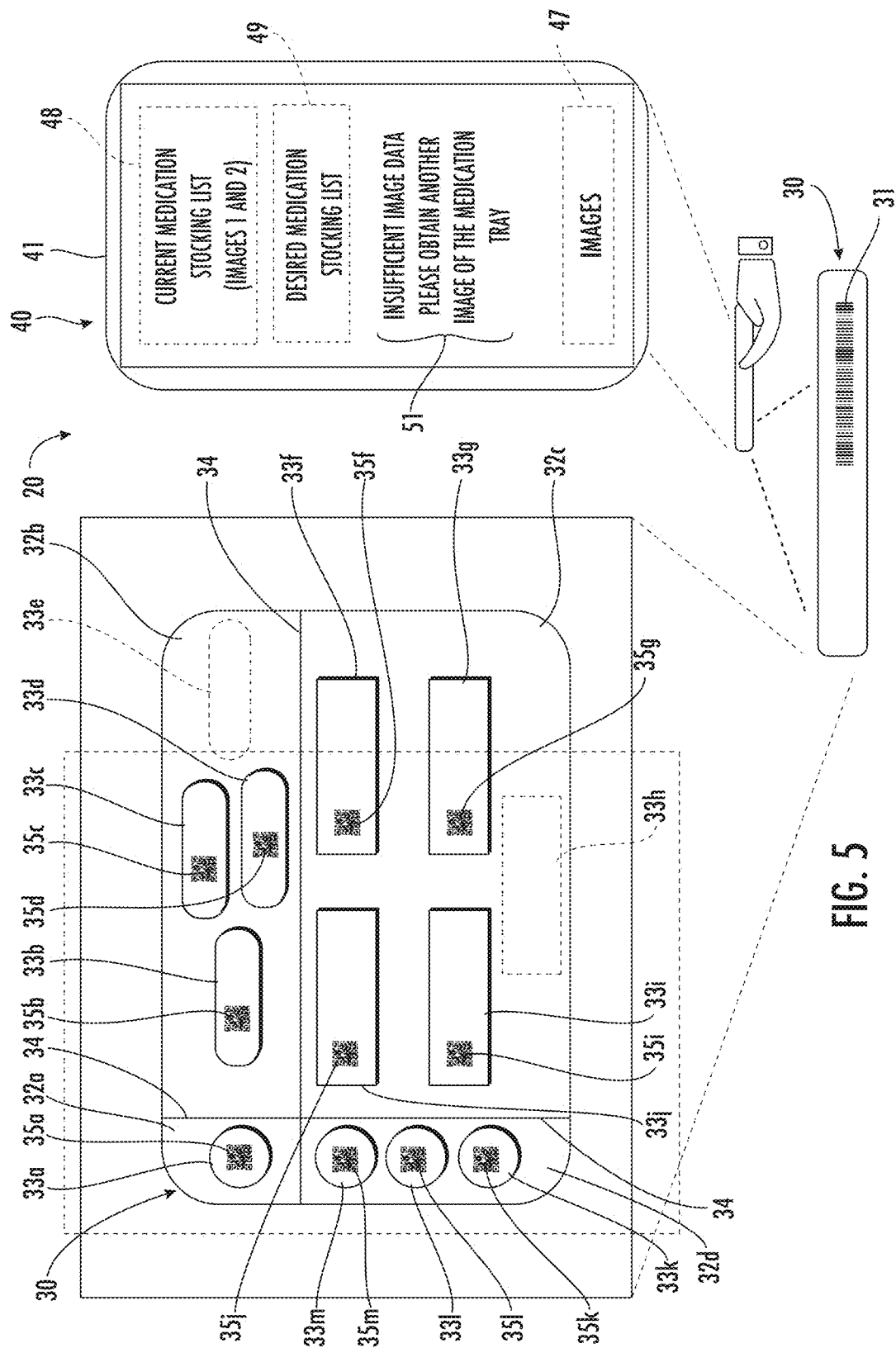
FIG. 5 is another schematic diagram of the medication inventory system in accordance with the embodiment of FIG. 4
Figure 6:
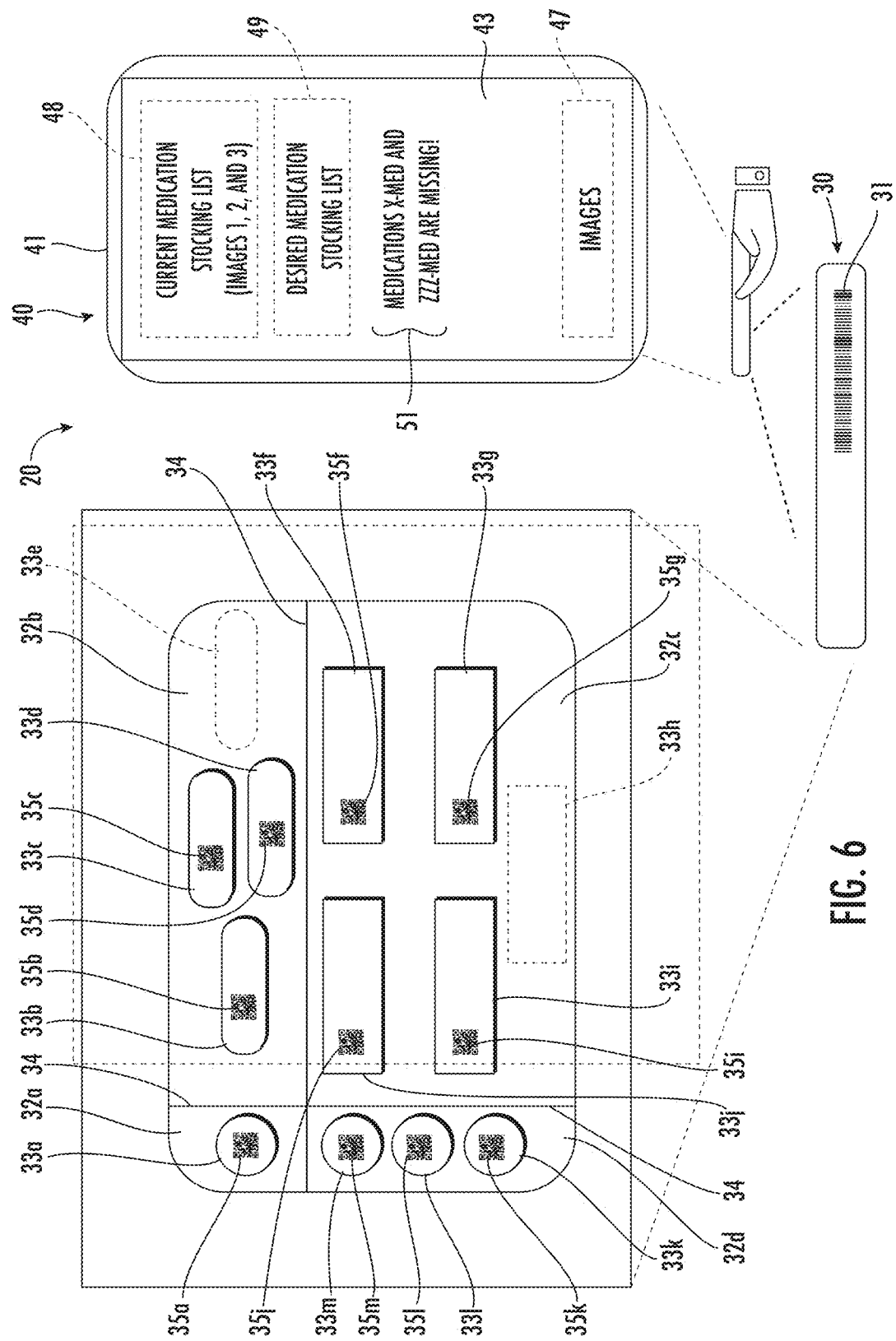
FIG. 6 is another schematic diagram of the medication inventory system in accordance with the embodiment of FIG. 4.
Figure 7:
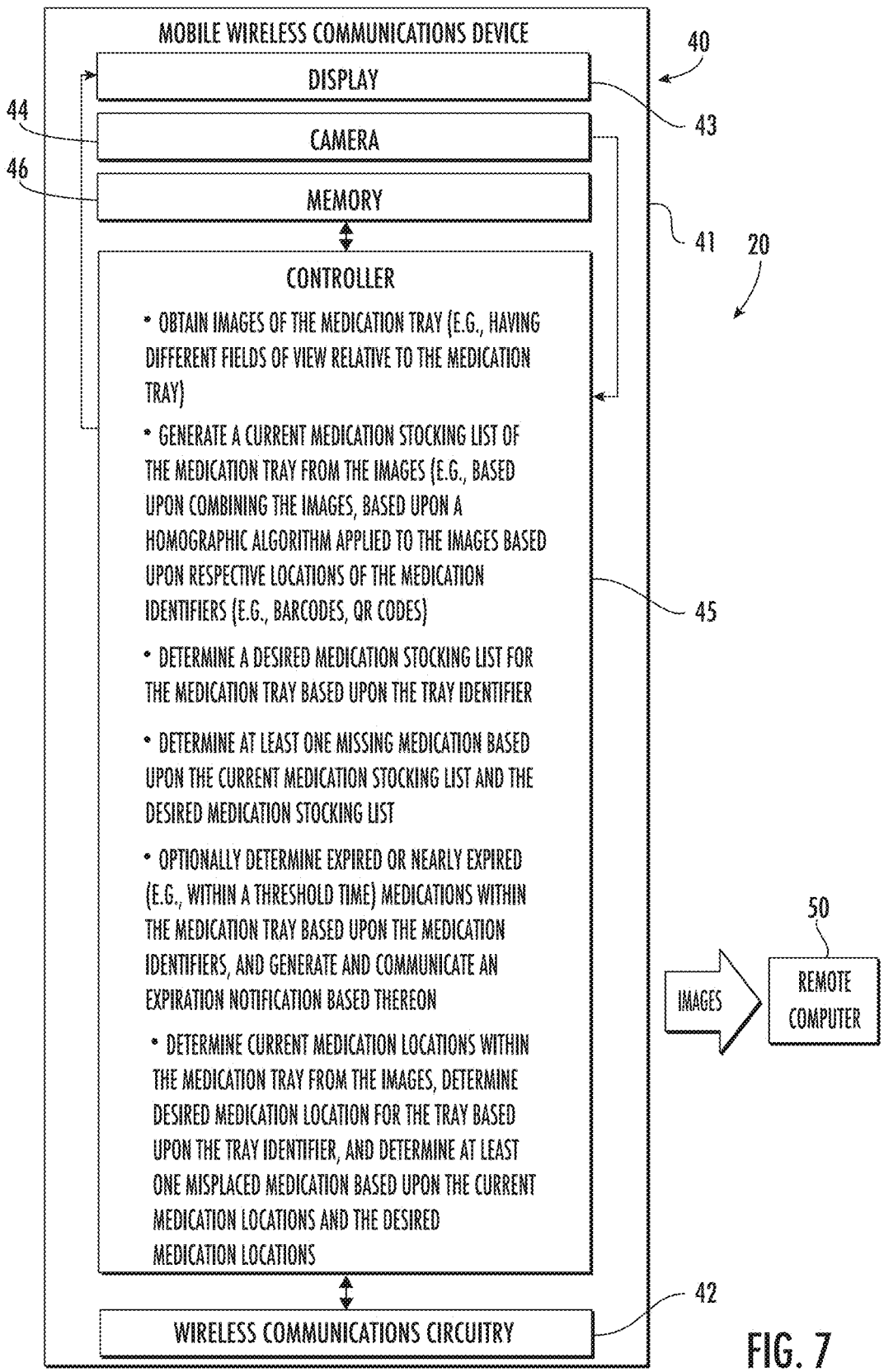
FIG. 7 is a schematic block diagram of the medication inventory system of FIG. 4.
Figure 9:
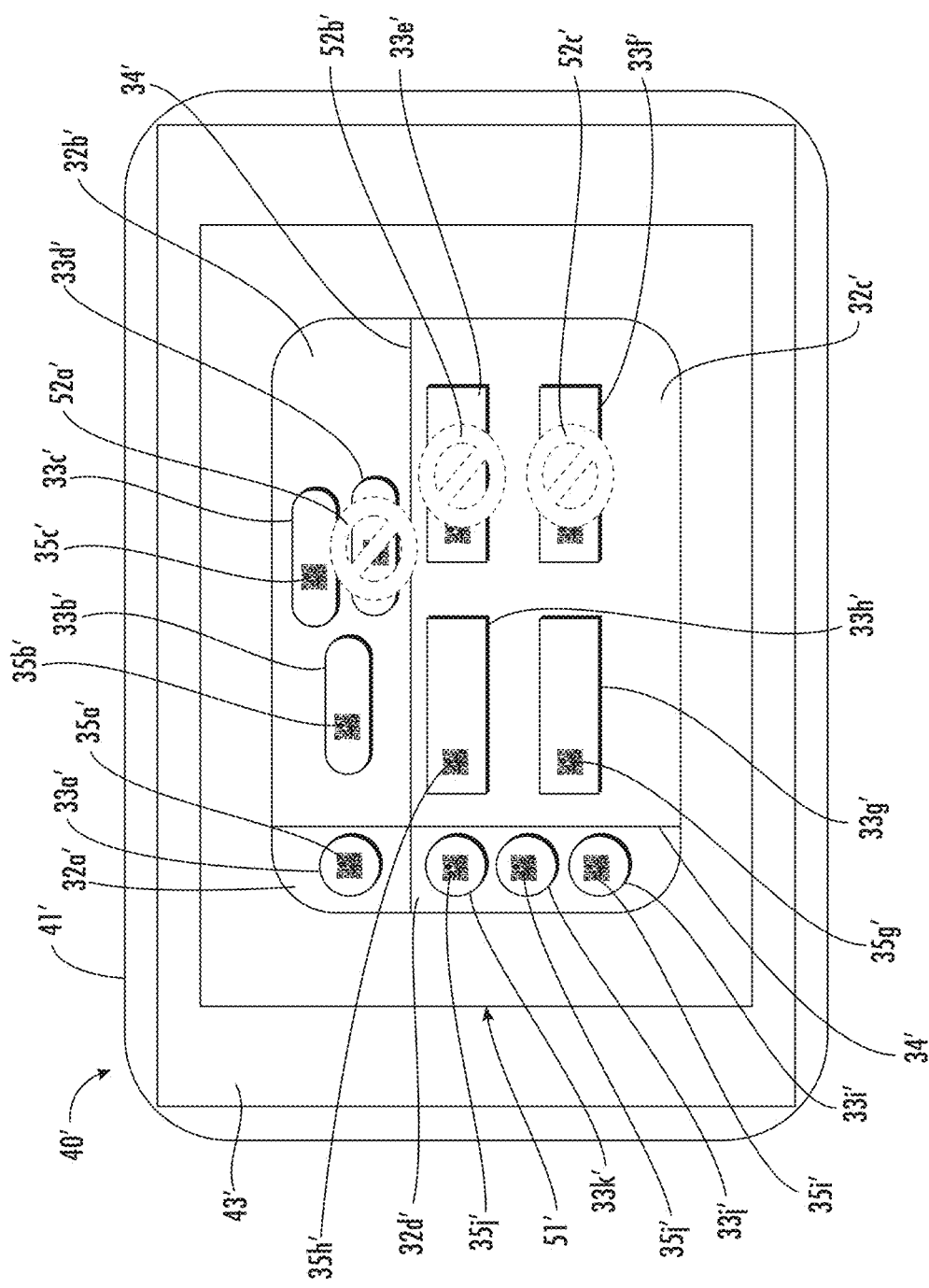
FIG. 9 is a schematic diagram of a mobile wireless communications device in accordance with another embodiment.

Moreover, a relative orientation of the mobile wireless communications device 40 to the medication tray 30 may result in some medication identifiers 35a-35n not being able to be read or decoded. Thus, the mobile wireless communications device 40 may generate a notification 51 as to whether a sufficient number of images has been obtained (FIGS. 5-6). Referring briefly to FIG. 9, in another embodiment, the notification 51' may be in the form of an image of the medication tray 30' on the display 43' of the mobile wireless communications device 40' and include indicia 52a'-52c', which may be color-coded, adjacent respective medications 33d'-33f' for which medication identifiers 35d'-35f' were unable to be identified or decoded.

At Block 166, the mobile wireless communications device 40 generates a current medication stocking list 48 of the medication tray 30 from the images 47. More particularly, the mobile wireless communications device 40 generates the current medication stocking list 48 based upon combining the images 47. For example, the mobile wireless communications device 40 may generate the current medication stocking list 48 based upon a homographic algorithm applied to the images 47, which may be based upon respective locations of the medication identifiers 35a-35n. An exemplary homographic algorithm, contrary to conventional homographic algorithms, does not use feature extraction or k-nearest-neighbor matching to provide the feature matches, but uses the individually identifiable identifiers (e.g., barcodes) already present in the process to provide feature matches, and as a result creates relatively consistent repeatable homographic processed images.

The mobile wireless communications device 40 determines a desired medication stocking list 49 of the medication tray 30 based upon the tray identifier 31 (Block 168), for example, using techniques along the lines described above. In some embodiments, desired medication stocking lists 49 for respective medication trays 30 may be stored in the memory 46 of the mobile wireless communications device 40.

The mobile wireless communications device 40, at Block 170, determines one or more missing medications 33e, 33h (e.g., that may have been used) based upon the current medication stocking list 48 and the desired medication stocking list 49. More particularly, if a medication that is part of the desired medication stocking list 49 is determined to not be in the current medication stocking list 48 (i.e., a medication 33e, 33h was not found in the combined images 47), a notification 51 may be generated and displayed on the display 43 of the mobile wireless communications device 40 and/or communicated. The notification 51 may be in the form of a list, for example, and/or an image of the medication tray with indicia (e.g. color-coded). The controller 45 may use image recognition techniques, for example, for identifying the medication identifiers 35a-35n, to determine missing medications. In some embodiments, the mobile wireless communications device 40 may determine that a medication is missing based upon there being less than a desired number (e.g., a threshold number) of medications in a given compartment.

In some embodiments, the mobile wireless communications device 40 may wirelessly communicate the images 47, either individually or combined, to a remote computer 50 for archiving and for auditing purposes (Block 172). The missing medications may also be wirelessly communicated to the remote computer 50. In some embodiments, the mobile wireless communications device 40 may generate and communicate an invoice for the missing medications. Alternatively or additionally, the mobile wireless communications device 40 may communicate the missing medications to a remote computer 50 for processing, for example, generation and communication of the invoices.

Figure 10:
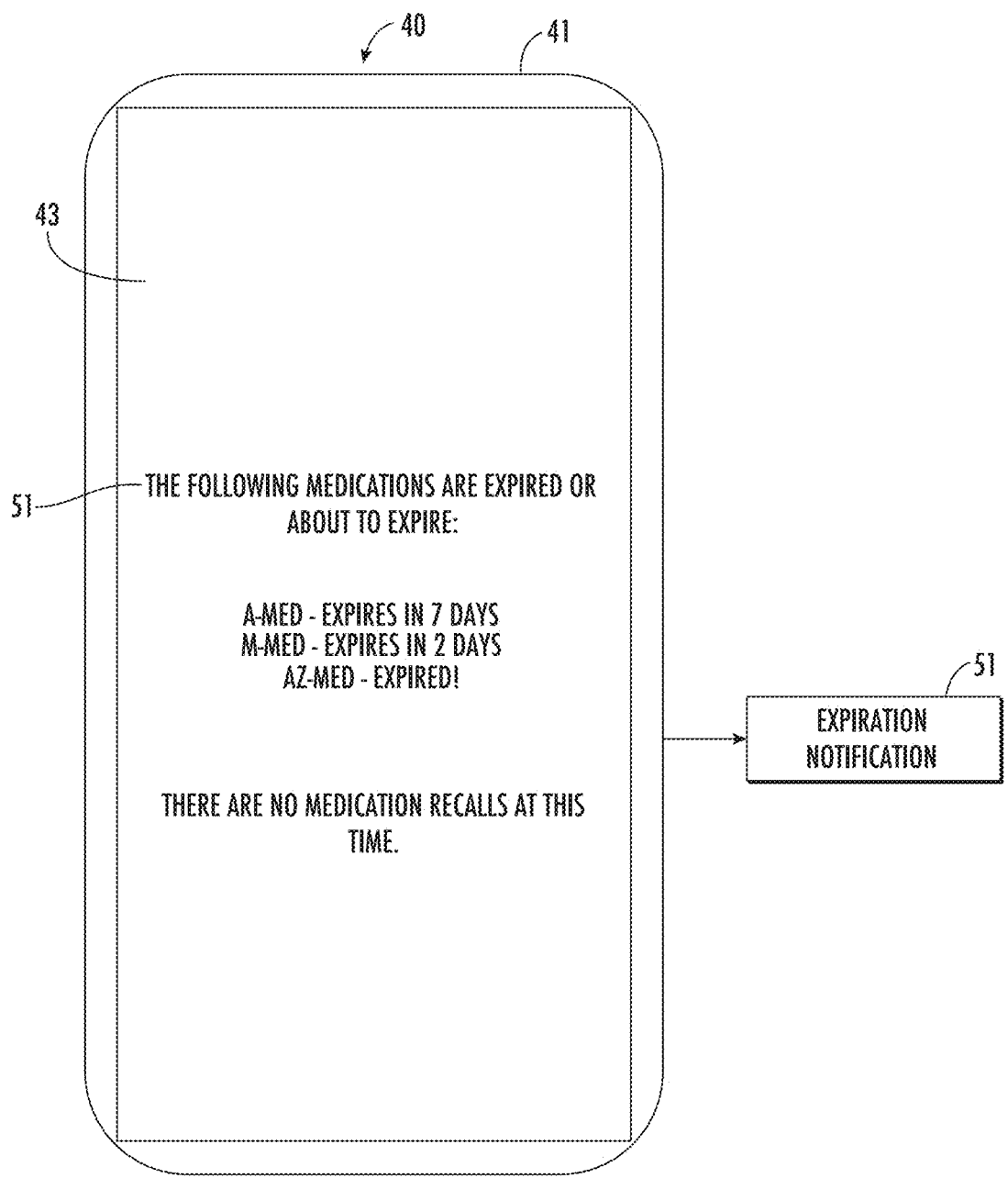
FIG. 10 is a schematic diagram of a mobile wireless communications device in accordance with an embodiment.

Referring now additionally to FIG. 10, the mobile wireless communications device 40 may also determine expired medications 33a-33n or nearly expired medications within the medication tray 30 based upon the medication identifiers 35a-35n (Block 174), for example, by comparing a lot number of the medication. The mobile wireless communications device 40 may generate an expiration notification 51 for display on the display 43 indicative of an expired medication or nearly expired medication (e.g., within a threshold time period from an actual expiration). The expiration notification 51 may also be communicated, for example, to a remote computer 50 or remote device. The mobile wireless communications device 40 may also determine recalled medications 33a-33n, for example, also based upon the lot number or other identifying information.

Figure 11:
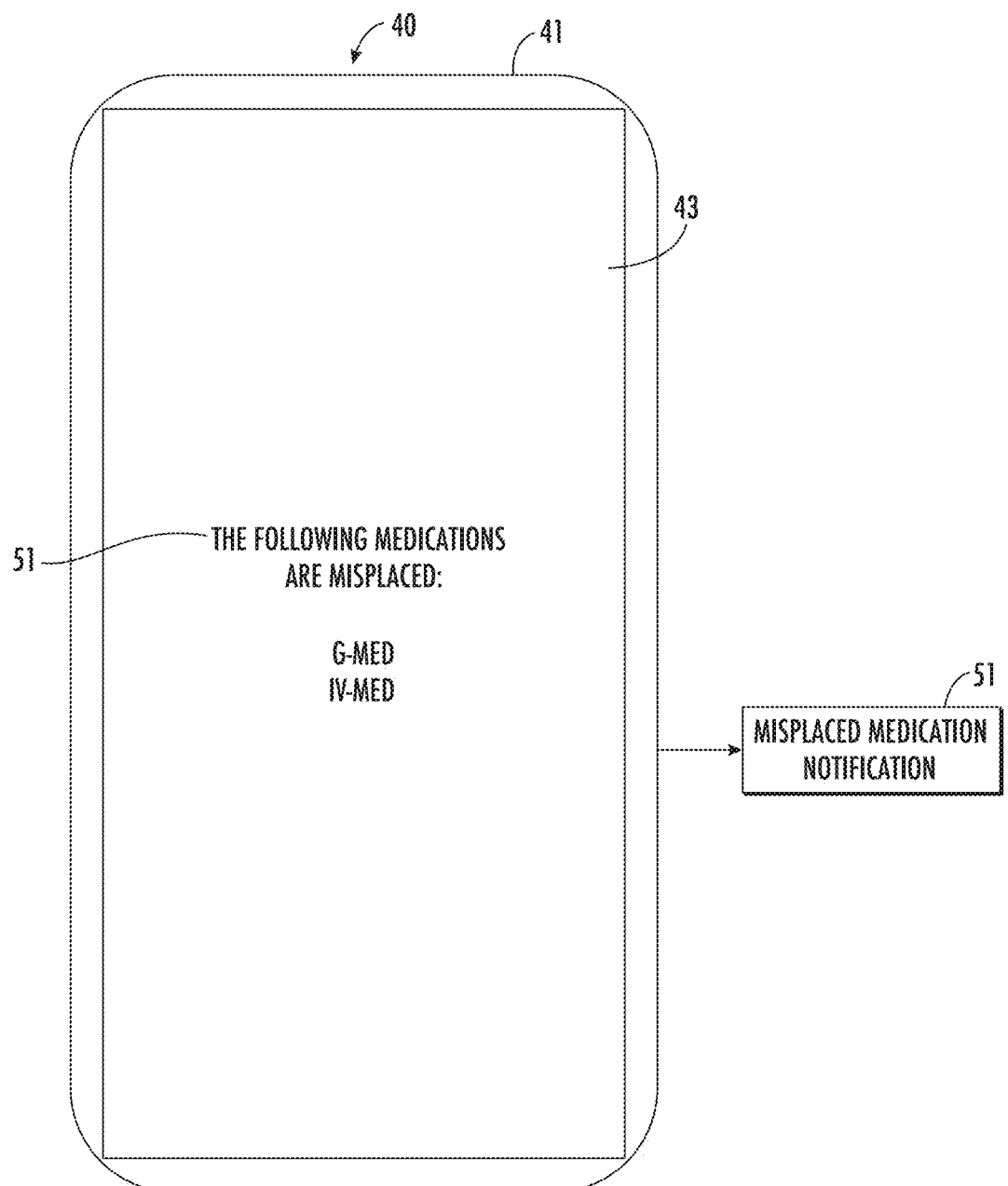
FIG. 11 is a schematic diagram of a mobile wireless communications device in accordance with an embodiment.

Referring now additionally to FIG. 11, the mobile wireless communications device 40 may determine one or more misplaced medications 33a-33n based upon current medication locations and desired medication locations (Block 176). More particularly, the mobile wireless communications device 40 may determine current medication locations within the medication tray 30 from the images 47 (e.g., based upon the medication identifiers 35a-35n) and determine desired medication locations for the tray based upon the tray identifier so that the misplaced medications are determined based upon the current medication locations and the desired medication locations. The mobile wireless communications device 40 may generate a misplaced medication notification 51 for display on the display 43 indicative of a misplaced medication (e.g., not in a correct compartment 32a-32n). The misplaced medication notification 51 may also be communicated, for example, to a remote computer 50 or remote device. In some embodiments, the medication tray 30 may be displayed on the display 43 of the mobile wireless communications device 40 along with the medications and indicia to indicate that one or more medications are misplaced. Operations end at Block 178.

As will be appreciated by those skilled in the art, the medication inventory system 20 may be particularly beneficial for ensuring hospital pharmaceutical trays are refilled efficiently and correctly using any of a variety of handheld device, for example. The medication inventory system 20 may integrate with current pharmacy safety/workflow and tracking technology, and provides pharmacy safety/workflow and tracking technology in a mobile or handheld form factor, thus supporting bring-your-own-device functionality.

Further details of medication trays and related processing of medications therein is described in U.S. patent application Ser. Nos. 16/448,493, 16/395,343, and 16/395,353, the entire contents of all of which is hereby incorporated by reference.

A method aspect is directed to a method of processing medication inventory in a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith. The method includes using a mobile wireless communications device 40 to obtain a plurality of images 47 of the medication tray 30 and generate a current medication stocking list 48 of the medication tray from the plurality of images. The method also includes using the mobile wireless communications device 40 to determine the desired medication stocking list 49 for the medication tray 30 based upon the medication tray identifier 31 and determine at least one missing medication 33a-33n based upon the current medication stocking list 48 and the desired medication stocking list.

A computer readable medium aspect is directed to a non-transitory computer readable medium for a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith, the non-transitory computer readable medium includes computer executable instructions that when executed by a controller 45 of a mobile wireless communications device 40 cause the controller to perform operations. The operations include obtaining a plurality of images 47 of the medication tray 30 and generating a current medication stocking list 48 of the medication tray from the plurality of images. The operations also include determining a desired medication stocking list 49 for the medication tray 30 based upon the tray identifier 31, and determining at least one missing medication 33a-33n based upon the current medication stocking list 48 and the desired medication stocking list.

Figure 12:
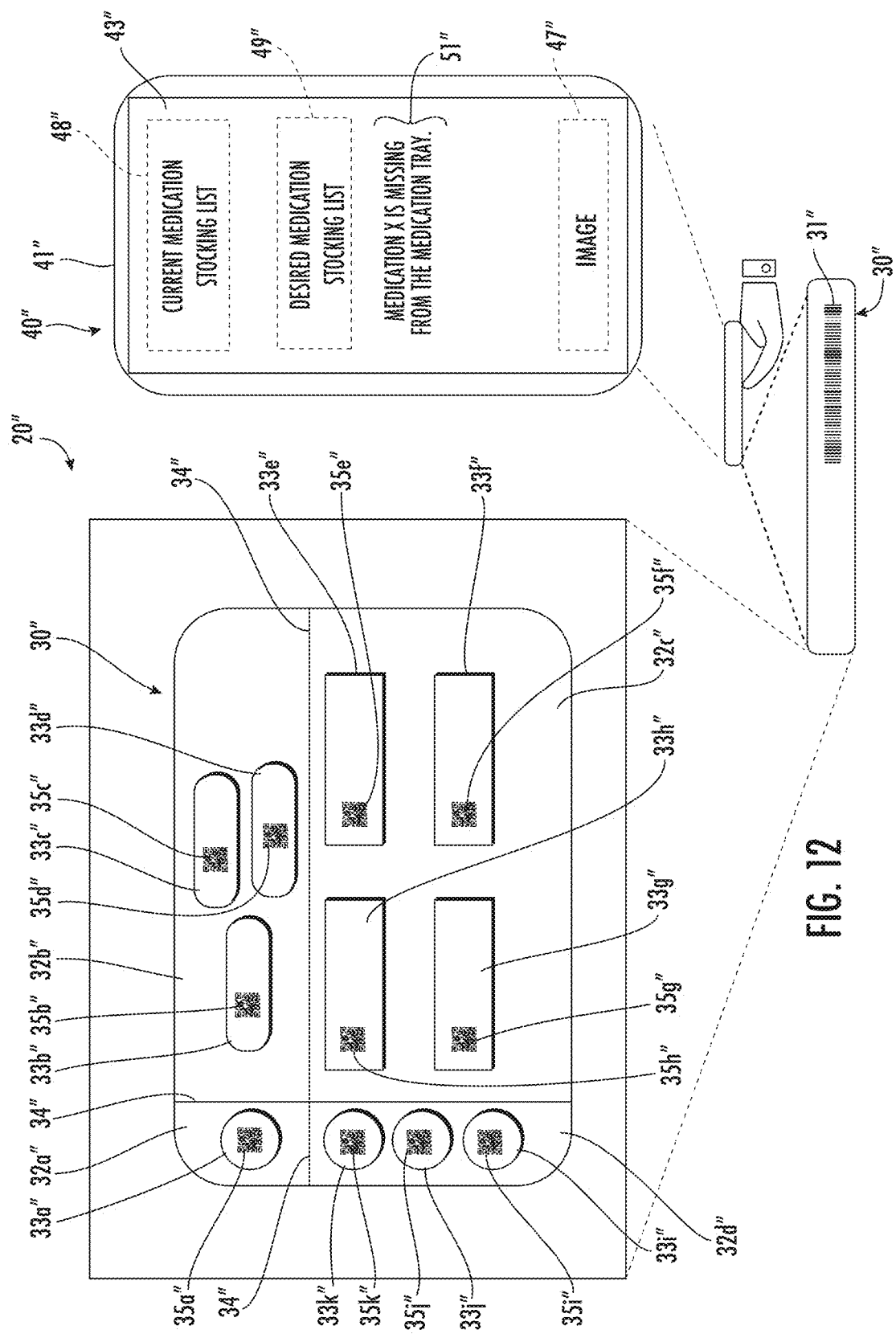
FIG. 12 is a schematic diagram of a medication inventory system in accordance with an embodiment.
Figure 13:
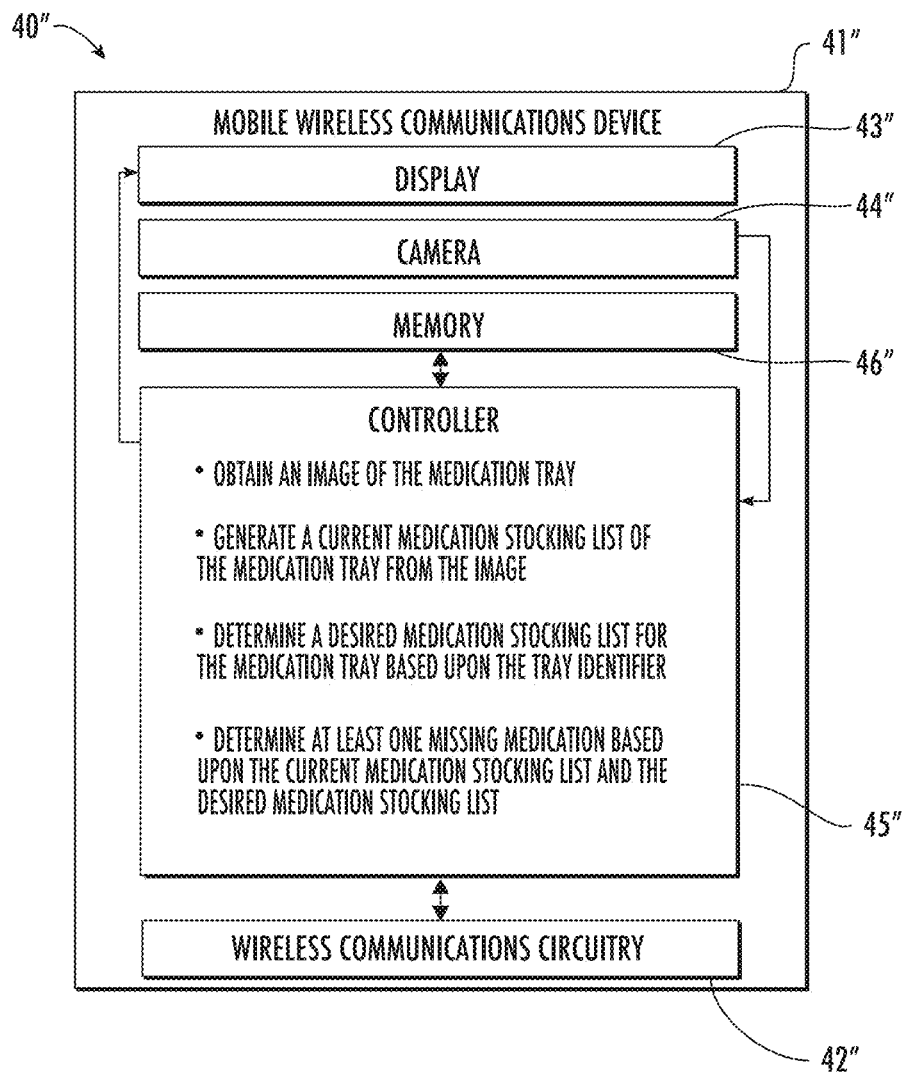
FIG. 13 is a schematic block diagram of the mobile wireless communications device of FIG. 12.

Referring now to FIGS. 12-13, in another embodiment, similar to the embodiments above, a medication inventory system 20" illustratively includes a medication tray 30". The medication tray 30" includes partitions 34" that define compartments 32a"-32n". Each compartment may store a medication 33a"-33n", multiple medications, a medical or medicated device, a medication container that includes individual medications therein, or other item or substance used for medical treatment. Each medication 33a"-33n" has a respective medication identifier 35a"-35n" associated therewith, for example, a barcode, quick-response (QR) code, alphanumeric characters, or other optically recognizable and unique code.

The medication tray 30" has a tray identifier 31" associated therewith. The tray identifier 31" may be in the form of a barcode, for example, that may be printed or applied (e.g., via an adhesive label) on the medication tray 30". The tray identifier 31" may be in the form of another type of identifier, for example, QR code, alphanumeric characters, or other optically recognizable and unique code.

The medication inventory system 20" also includes a mobile wireless communications device 40", illustratively in the form of a smartphone and similar to the embodiments described above. Similarly to the mobile wireless communications device described above, the mobile wireless communications device 40" illustratively includes a housing 41" and wireless communications circuitry 42" carried by the housing. The mobile wireless communications device 40" also includes a display 43", for example, a touch display, carried by the housing 41". A controller 45" is coupled to the wireless communications circuitry 42" and the display 43". A camera 44" is also carried by the housing 41" and coupled to the controller 45". One or more input devices may be carried by the housing 41" and coupled to the controller 45". While the mobile wireless communications device 40" is illustratively in the form of a smartphone, the mobile wireless communications device may be in the form of a tablet, laptop computer, or wearable device, for example.

Figure 14:
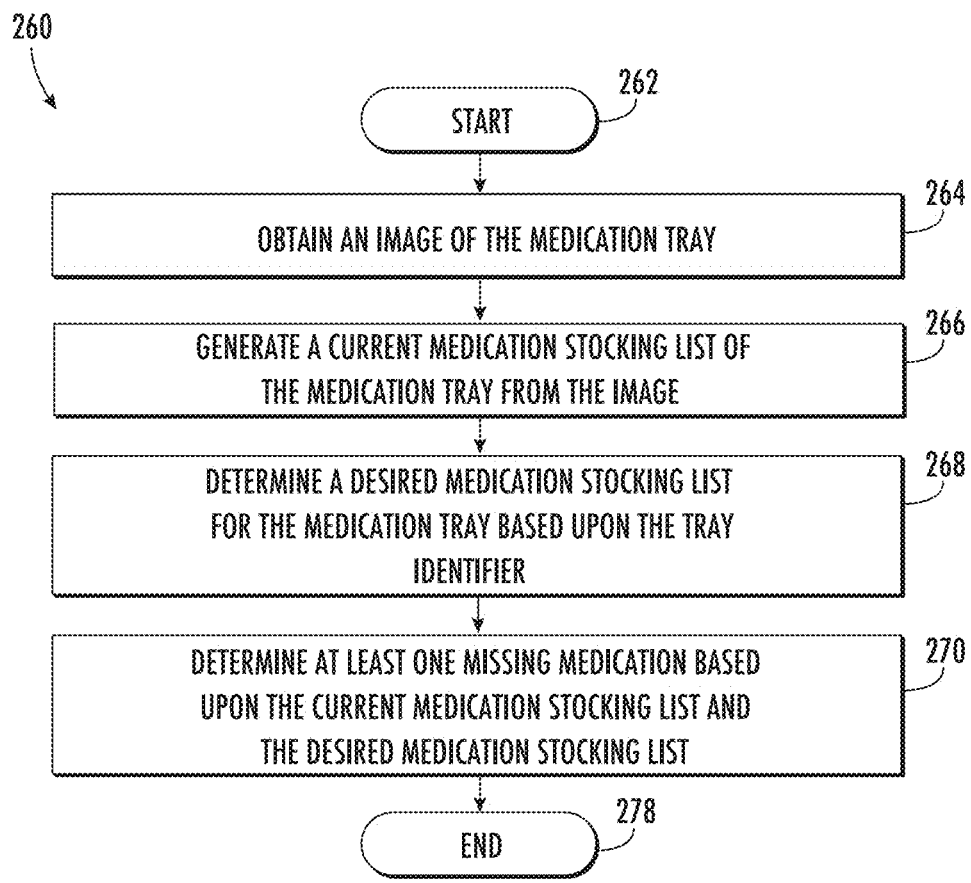
FIG. 14 is a flow diagram illustrating operation of the mobile wireless communications device of FIG. 13.

Referring now additionally to the flowchart 260 in FIG. 14, beginning at Block 262, operations of the mobile wireless communications device 40" of the medication inventory system 20" according to the present embodiments will now be described. At Block 264, the mobile wireless communications device 40" obtains an image 47", for example, a single image, of the medication tray 30". At Block 266, the mobile wireless communications device 40" generates a current medication stocking list 48" of the medication tray 30" from the image 47".

The mobile wireless communications device 40" determines a desired medication stocking list 49" of the medication tray 30" based upon the tray identifier 31" (Block 268). More particularly, the mobile wireless communications device 40" may obtain the desired medication stocking list 49" from a remote computer or database based upon the tray identifier 31". In other words, the tray identifier 31" may be used as an index to retrieve or obtain the desired medication stocking list 49".

The mobile wireless communications device 40", at Block 270, determines one or more missing medications 33e", 33h" based upon the current medication stocking list 48" and the desired medication stocking list 49". More particularly, if a medication 33a"-33n" that is part of the desired medication stocking list 49" is determined to not be in the current medication stocking list 48" (i.e., a medication was not found in the image 47"), a notification 51" may be generated and displayed on the display 43" of the mobile wireless communications device 40". The controller 45" may use image recognition techniques, for example, for identifying the medication identifiers 35a"-35n", to determine missing medications. Operations end at Block 278.

Figure 15:
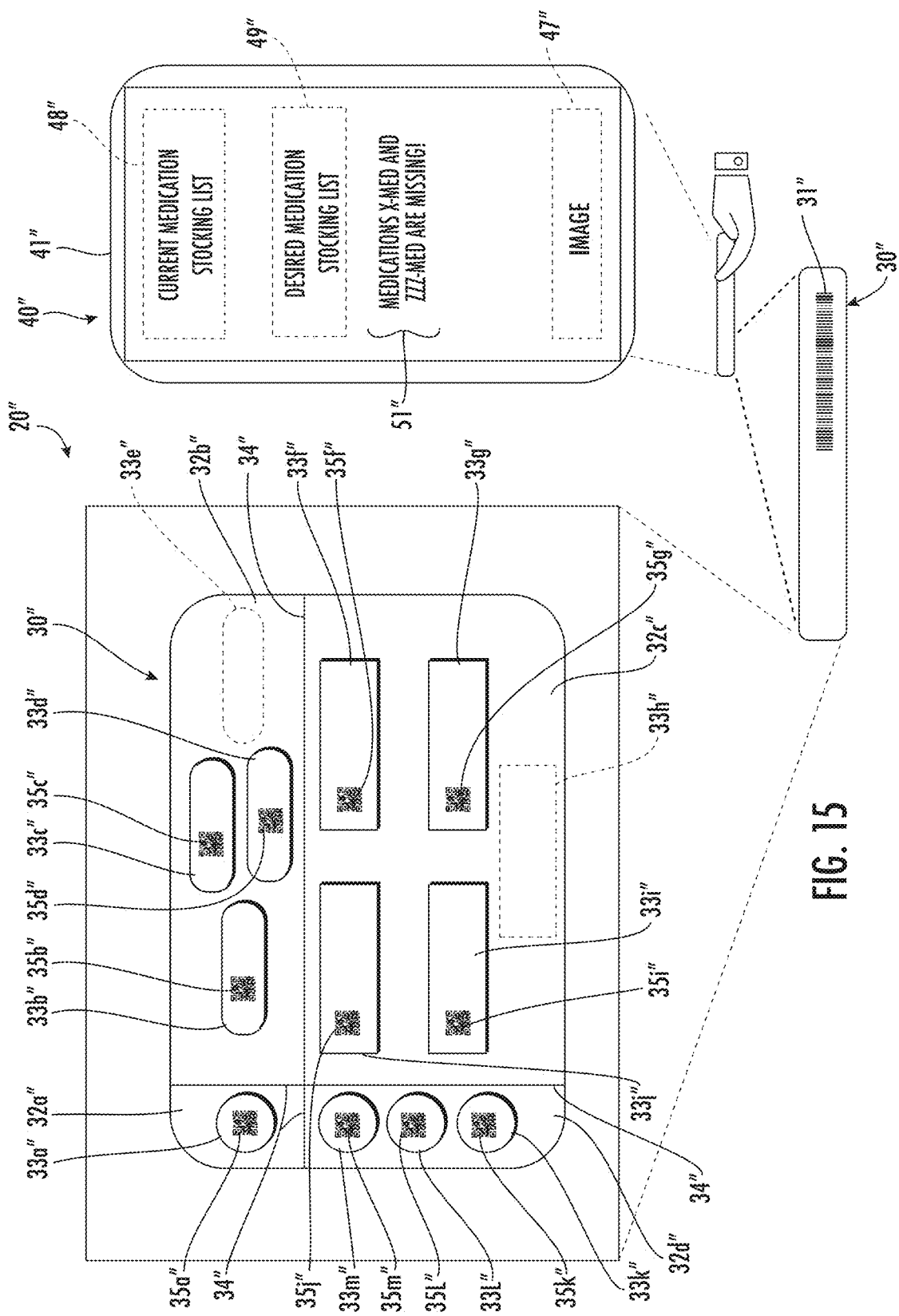
FIG. 15 is a schematic diagram of a medication inventory system in accordance with an embodiment.
Figure 16:
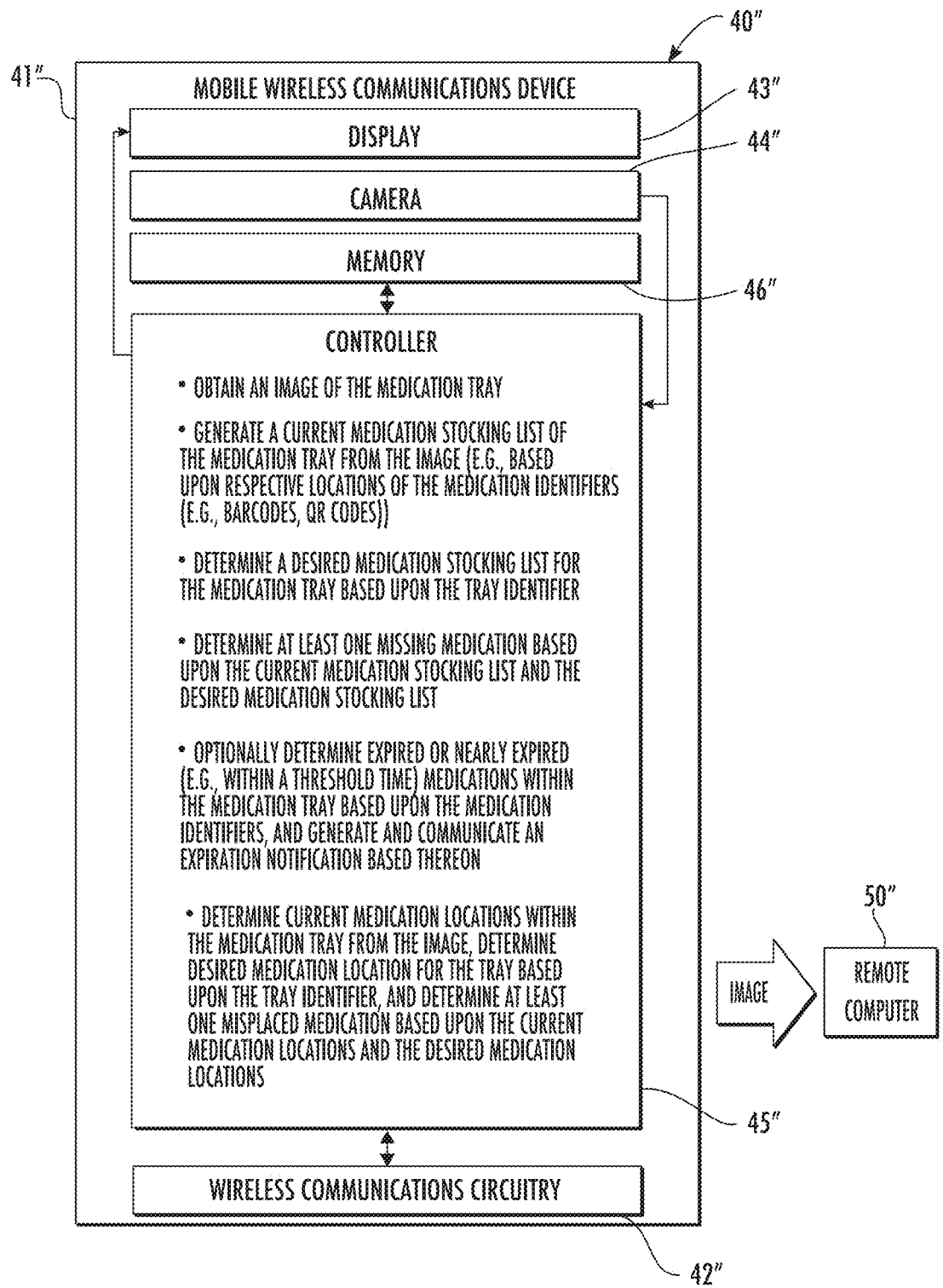
FIG. 16 is a schematic block diagram of a portion of the mobile wireless communications device of FIG. 15 including a remote device.
Figure 17:
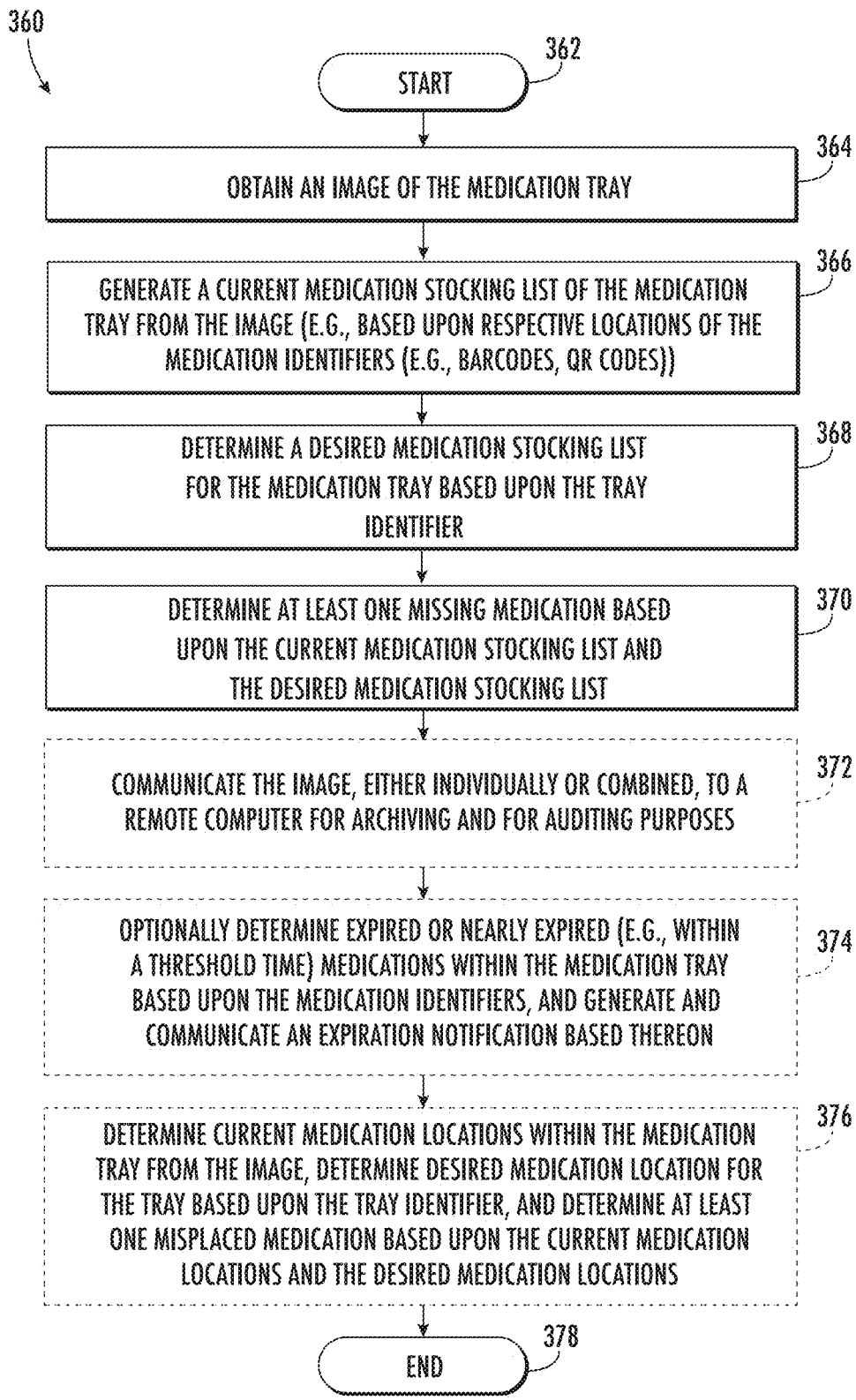
FIG. 17 is a flow diagram illustrating operation of the mobile wireless communications device of FIG. 16.

Referring now to FIGS. 15-16, and the flowchart 360 in FIG. 17, beginning at Block 362 more detailed operations of the mobile wireless communications device 40" with respect to the medication inventory system 20" will now be described. At Block 364, the mobile wireless communications device 40" obtains a single image 47" of the medication tray 30". The image 47" may include, in its field-of-view, the entire medication tray 30". In other words, a given user captures, via the camera 44", an image that includes the entire medication tray 30" or sufficient portion thereof to identify or generate the current medication stocking list 48". For example, edges of the medication tray 30" may be cut-off in the image 47". The image 47" may be obtained from the camera 44" at an orientation that may not be "straight-on", for example. As will be appreciated by those skilled in the art, however, it may be desirable that the single image 47" have a high enough resolution so that both the tray and medication identifiers 31", 35a"-35n" are legible or readable. Thus, it may be desirable to position the mobile wireless communications device 40" including the camera 44" relatively close to the medication tray 30" so that the entire medication tray is included in the image 47" or field of view, but not too far away as to provide a lower resolution of the medications 33a"-33n".

At Block 366, the mobile wireless communications device 40" generates a current medication stocking list 48" of the medication tray 30" from the single image 47". More particularly, the mobile wireless communications device 40" generates the current medication stocking list 48" based upon an image analysis of the image 47". For example, the mobile wireless communications device 40" may generate the current medication stocking list 48" based upon known boundaries, shapes, and other identifiers within the image, which may be based upon respective locations of the medication identifiers 35a"-35n".

The mobile wireless communications device 40" determines a desired medication stocking list 49" of the medication tray 30" based upon the tray identifier 31' (Block 368), for example, using techniques along the lines described above. In some embodiments, desired medication stocking lists 49" for respective medication trays 30" may be stored in the memory 46" of the mobile wireless communications device 40".

The mobile wireless communications device 40", at Block 370, determines one or more missing medications 33e", 33h" (e.g., that may have been used) based upon the current medication stocking list 48" and the desired medication stocking list 49". More particularly, if a medication 33a"-33n" that is part of the desired medication stocking list 49" is determined to not be in the current medication stocking list 48" (i.e., a medication 33e", 33h" was not found in the single image 47"), a notification 51" may be generated and displayed on the display 43" of the mobile wireless communications device 40" and/or communicated. The notification 51" may be in the form of a list, for example, and/or an image of the medication tray with indicia (e.g. color-coded). The controller 45" may use image recognition techniques, for example, for identifying the medication identifiers 35a"-35n", to determine missing medications. In some embodiments, the mobile wireless communications device 40" may determine that a medication 33a"-33n" is missing based upon there being less than a desired number (e.g., a threshold number) of medications in a given compartment 32a"-32n".

In some embodiments, the mobile wireless communications device 40" may wirelessly communicate the single image 47" to a remote computer 50" for archiving and for auditing purposes (Block 372). The missing medications 33e", 33h" may also be wirelessly communicated to the remote computer 50". In some embodiments, the mobile wireless communications device 40" may generate and communicate an invoice for the missing medications 33e", 33h". Alternatively or additionally, the mobile wireless communications device 40" may communicate the missing medications 33e", 33h" to a remote computer 50" for processing, for example, generation and communication of the invoices.

Similar to embodiments described above, the mobile wireless communications device 40" may also determine expired medications 33a"-33n" or nearly expired medications within the medication tray 30" based upon the medication identifiers 35a"-35n" (Block 374), for example, by comparing a lot number of the medication. The mobile wireless communications device 40" may generate an expiration notification 51" for display on the display 43" indicative of an expired medication or nearly expired medication (e.g., within a threshold time period from an actual expiration). The expiration notification 51" may also be communicated, for example, to a remote computer 50" or remote device. The mobile wireless communications device 40" may also determine recalled medications 33a"-33n", for example, also based upon the lot number or other identifying information.

The mobile wireless communications device 40" may also determine one or more misplaced medications 33a'-33n" based upon current medication locations and desired medication locations (Block 376). More particularly, the mobile wireless communications device 40" may determine current medication locations within the medication tray 30" from the single image 47" (e.g., based upon the medication identifiers 35a"-35n') and determine desired medication locations for the tray based upon the tray identifier 31" so that the misplaced medications are determined based upon the current medication locations and the desired medication locations. The mobile wireless communications device 40" may generate a misplaced medication notification 51" for display on the display 43" indicative of a misplaced medication (e.g., not in a correct compartment 32a"-32n"). The misplaced medication notification 51" may also be communicated, for example, to a remote computer 50" or remote device. In some embodiments, the medication tray 30" may be displayed on the display 43" of the mobile wireless communications device 40" along with the medications 33a"-33n" and indicia to indicate that one or more medications are misplaced. Operations end at Block 378.

In some embodiments, the mobile wireless communications device 40" may determine that the single image 47" is not sufficient and may then prompt the user to obtain one or more additional images, for example, of a portion or portions of the medication tray 30" and/or at varying fields of view. More particularly, the mobile wireless communications device 40" may perform a single-image analysis as noted above, and then, if the single-image analysis is insufficient, the mobile wireless communications device may either switch to the multi-image analysis described herein, or supplement the single image with the additional images, for example, by stitching images, overlaying images, or other image processing techniques, so that the overall or combined images are sufficient to generate the current medication list.

A method aspect is directed to a method of processing medication inventory in a medication inventory system 20" that includes a medication tray 30" including a plurality of compartments 32a"-32n" for storing respective medications 33a"-33n" with each medication having a respective medication identifier 35a"-35n" associated therewith. The medication tray 30" has a tray identifier 31" associated therewith. The method includes using a mobile wireless communications device 40" to obtain an image 47" of the medication tray 30", generate a current medication stocking list 48" of the medication tray from the image, and determine a desired medication stocking list 49" for the medication tray based upon the tray identifier 31". The method also includes using the mobile wireless communications device 40" to determine at least one missing medication 33e", 33h" based upon the current medication stocking list 48" and the desired medication stocking list 49".

A computer readable medium aspect is directed to a non-transitory computer readable medium for a medication inventory system 20" that includes a medication tray 30" including a plurality of compartments 32a"-32n" for storing respective medications 33a"-33n" with each medication having a respective medication identifier 35a"-35n" associated therewith. The medication tray 30" has a tray identifier 31" associated therewith. The non-transitory computer readable medium includes computer executable instructions that when executed by a controller 45" of a mobile wireless communications device 40" cause the controller to perform operations. The operations include obtaining an image 47" of the medication tray 30", generating a current medication stocking list 48" of the medication tray from the image, and determining a desired medication stocking list 49" for the medication tray based upon the tray identifier 31". The operations also include determining at least one missing medication 33e", 33h" based upon the current medication stocking list 48" and the desired medication stocking list 49".

Referring now to FIGS. 18-21, in another embodiment, a medication inventory system 420 includes a medication tray 430 that includes compartments 432a-432k, defined by partitions 434, for storing respective medications 433a-433k. Similar to the embodiments described above, each compartment may store a medication 433a-433k, multiple medications, a medical or medicated device, a medication container that includes individual medications therein, or other item or substance used for medical treatment. For example, the medication tray 430 may be part of a crash cart, as will be appreciated by those skilled in the art. Of course, the medication tray 430 may be used in other medical environments, for example, an examination room, emergency room, treatment room, operating room, etc. For example, the medication tray 430 may be in the form of a drawer within a medication cabinet or medication dispensing cabinet. Each medication 433a-433k has a respective medication identifier 435a-435k associated therewith, for example, a barcode, quick-response (QR) code, alphanumeric characters, or other optically recognizable and unique code.

The medication tray 430 includes a boundary wall 436 that defines a boundary outline 456 of the medication tray. More particularly, the boundary wall 436 includes first and second opposing perimeter walls that define the boundary outline. In some embodiments, for example, where the medication tray 430 has a round shape, there may be only a single boundary wall 436.

The medication inventory system 420 also includes boundary markers 438 that are illustratively carried by the boundary wall 436. Each boundary marker 438 includes a body 452 having a slot (e.g., a slotted based defined by two legs 454a, 454b) that is slidably positioned on the boundary wall 436. On an upper surface of each boundary marker 438 is a machine readable indicia 453. The indicia 453 may be in the form of an adhesive label or sticker having colored shapes thereon, different from the color of the boundary wall 436, that are detectable by a camera, for example, in a variety of lighting conditions and orientations. The upper surface of each boundary marker 438, which defines a top edge, is about 4 mm wide, which is sized to permit the machine readable indicia 453 to be shown along with a boundary region, for example, boundary "black" region. Of course, other types and sizes of coded boundary markers 438 may be used, for example, the sizing of which may be dependent on the algorithm used. The machine readable indicia 453 may include first and second color segments 411, 412, as will be described in further detail below.

Also, similarly to the above-described embodiments, the medication tray 430 has a tray identifier 431 associated therewith. The tray identifier 431 may be in the form of a barcode, for example, that may be printed or applied (e.g., via an adhesive label) on the medication tray 430. The tray identifier 431 may be in the form of another type of identifier, for example, QR code, alphanumeric characters, or other optically recognizable and unique code.

The medication inventory system 420 also includes a mobile wireless communications device 440, illustratively in the form of a smartphone. The mobile wireless communications device 440 illustratively includes a housing 441 and wireless communications circuitry 442 carried by the housing. The mobile wireless communications device 440 also includes a display 443, for example, a touch display, carried by the housing 441. A controller 445 is coupled to the wireless communications circuitry 442 and the display 443. A camera 444 is also carried by the housing 441 and coupled to the controller 445. One or more input devices may be carried by the housing 441 and coupled to the controller 445. While the mobile wireless communications device 440 is illustratively in the form of a smartphone, the mobile wireless communications device may be in the form of a tablet, laptop computer, or wearable device, for example.

Figure 22:
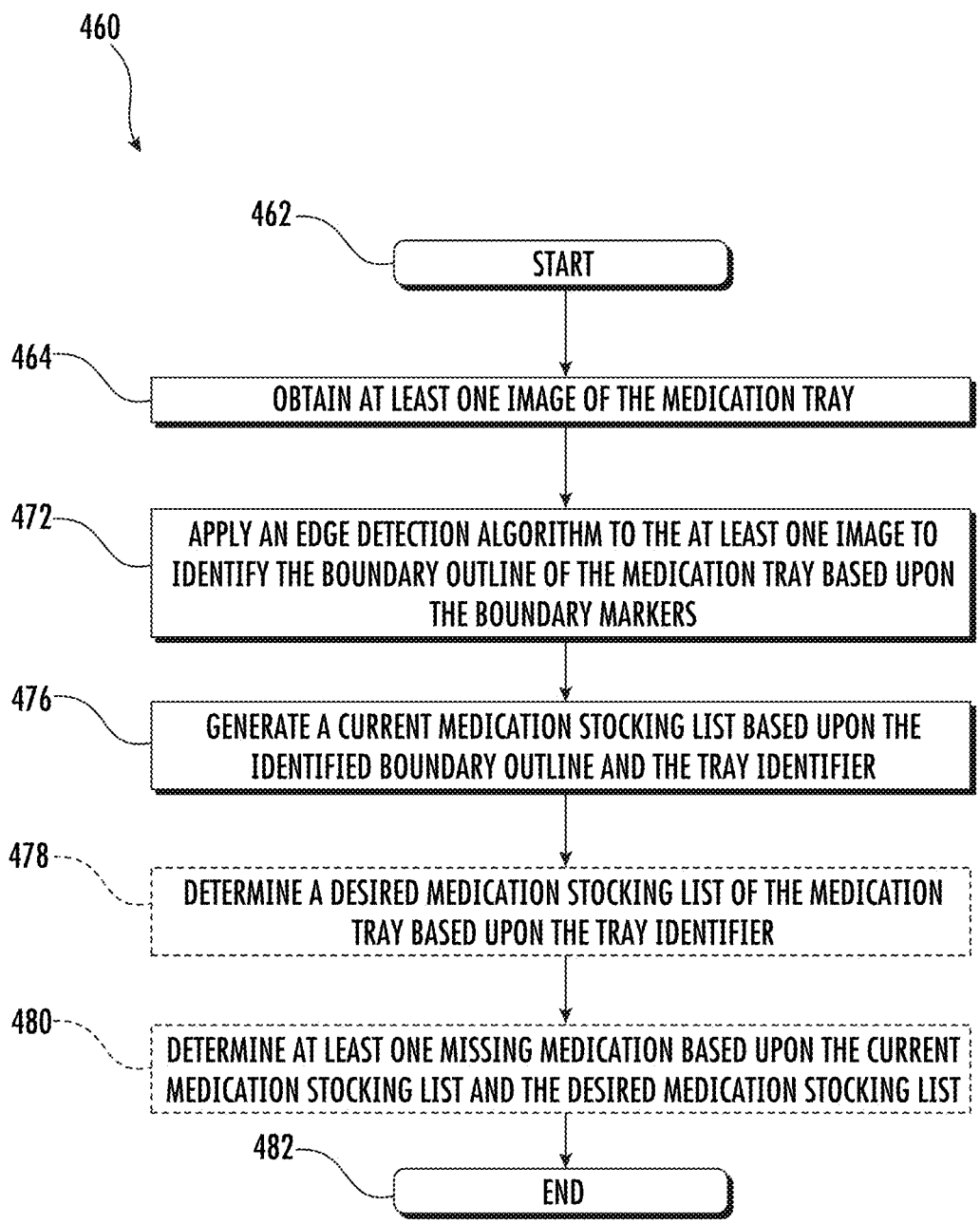
FIG. 22 is a flow diagram illustrating operation of the mobile wireless communications device of FIG. 18.
Figure 23:
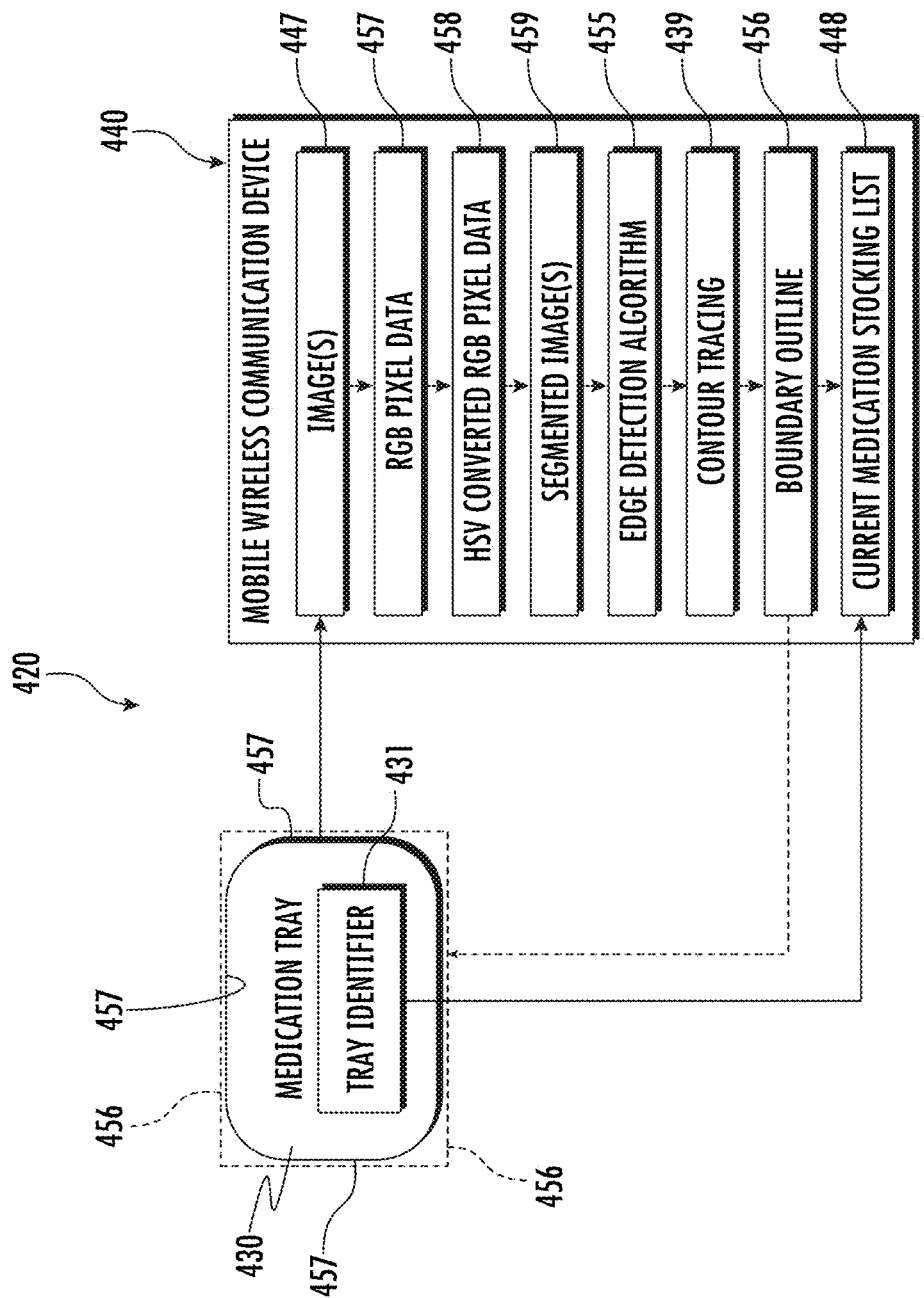
FIG. 23 is a schematic diagram of a medication inventory system in accordance with another embodiment.
Figure 24:
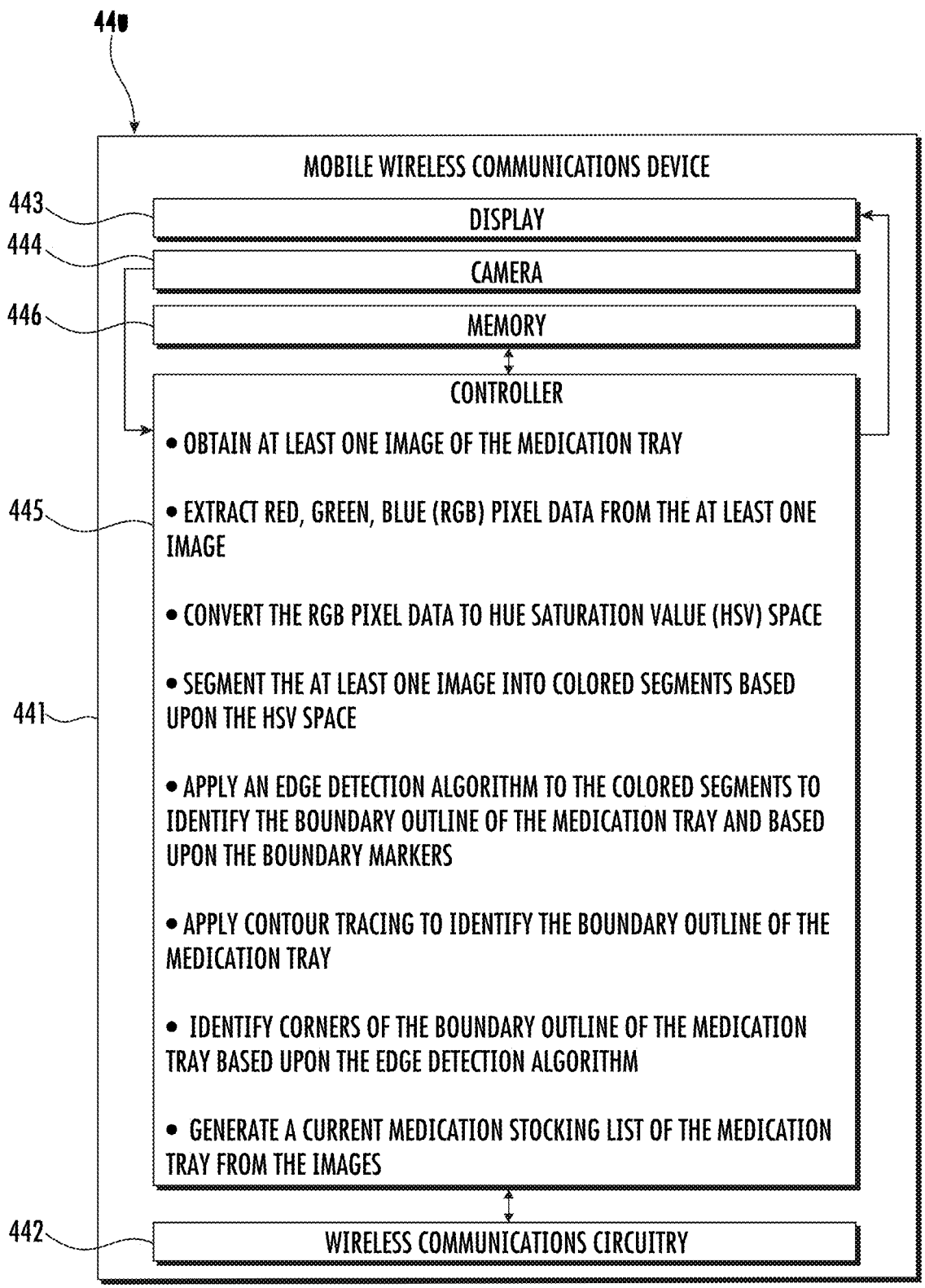
FIG. 24 is a schematic block diagram of the mobile wireless communications device of FIG. 23.

Referring now additionally to the flowchart 460 in FIG. 22, beginning at Block 462, operations of the mobile wireless communications device 440 of the medication inventory system 420 will now be described. While operations of the mobile wireless communications device 440 are described, it will be appreciated by those skilled in the art that the controller 445 and an associated memory 446 cooperate to perform the operations.

At Block 464 the mobile wireless communications device 440 obtains one or more images 447 of the medication tray 430. At Block 472 the mobile wireless communications device 440 applies an edge detection algorithm 455 to the obtained image 447 to identify the boundary outline 456 of the medication tray 430 based upon the boundary markers 438.

At Block 476, the mobile wireless communications device 440 generates a current medication stocking list 448 of the medication tray 430 based upon the identified boundary outline 456 and the tray identifier 431 from the one or more images 447. More particularly, the mobile wireless communications device 440 generates the current medication stocking list 448 similarly to the operations described above, but also generates the current medication stocking list based upon the boundary outline 456. Those skilled in the art will appreciate that by basing the current medication stocking list based upon the boundary outline 456, a more accurate and quicker processing time to generate the current medication stocking list 448 may be obtained since the controller 445 may not process parts of the image outside the boundary outline 456.

The mobile wireless communications device 440 may determine a desired medication stocking list 449 of the medication tray 430 based upon the tray identifier 431 (Block 478), for example, using techniques along the lines described above. In some embodiments, desired medication stocking lists 449 for respective medication trays 430 may be stored in the memory 446 of the mobile wireless communications device 440.

The mobile wireless communications device 440, at Block 480, may determine one or more missing medications (e.g., that may have been used) based upon the current medication stocking list 448 and the desired medication stocking list 449. More particularly, if a medication that is part of the desired medication stocking list 449 is determined to not be in the current medication stocking list 448 (i.e., a medication was not found in the at least one image 447), a notification 451 may be generated and displayed on the display 443 of the mobile wireless communications device 440 and/or communicated. The notification 451 may be in the form of a list, for example, and/or an image of the medication tray with indicia (e.g. color-coded). The controller 445 may use image recognition techniques, for example, for identifying the medication identifiers 435a-435n, to determine missing medications. In some embodiments, the mobile wireless communications device 440 may determine that a medication is missing based upon there being less than a desired number (e.g., a threshold number) of medications in a given compartment.

In some embodiments, the mobile wireless communications device 440 may also determine expired medications or nearly expired medications within the medication tray 430 based upon the medication identifiers 435a-435n. The operations of the mobile wireless communications device 440 with respect to determining expired medications are described above. Operations end at Block 482.

Figure 30:
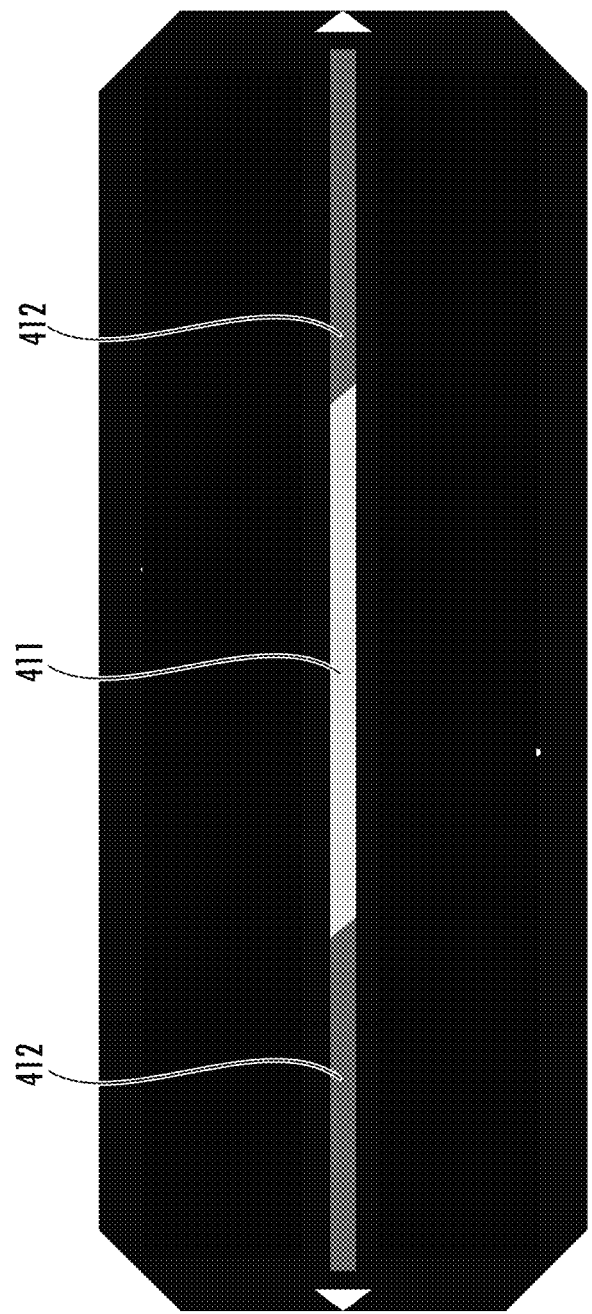
FIG. 30 is a schematic diagram of an upper surface of a boundary marker including a coded indicia in accordance with an embodiment.
Figure 31:
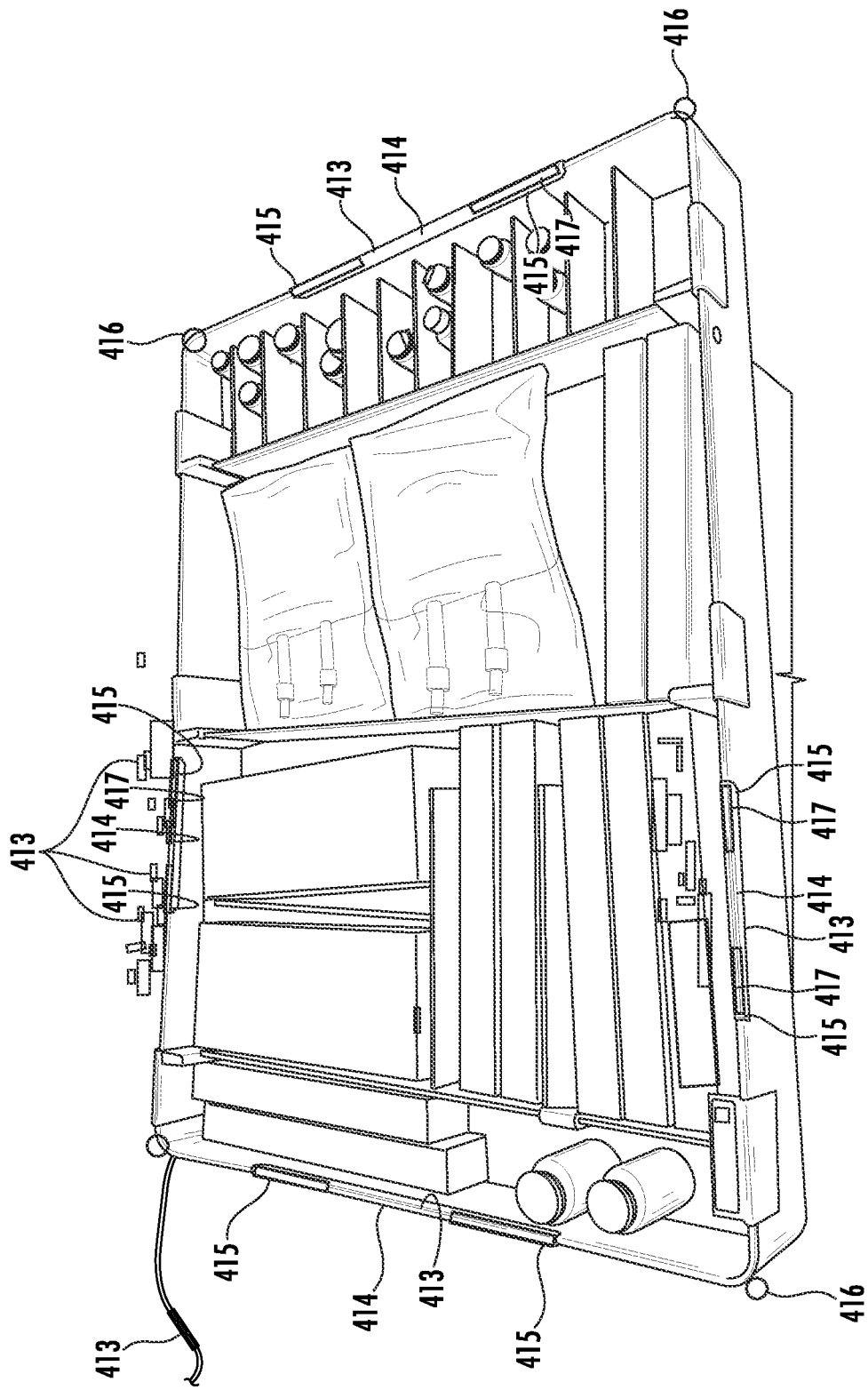
FIG. 31 is an exemplary image of a medication tray illustrating a visualization of identified edges and corners using the medication inventory system in accordance with an embodiment.
Figure 32:
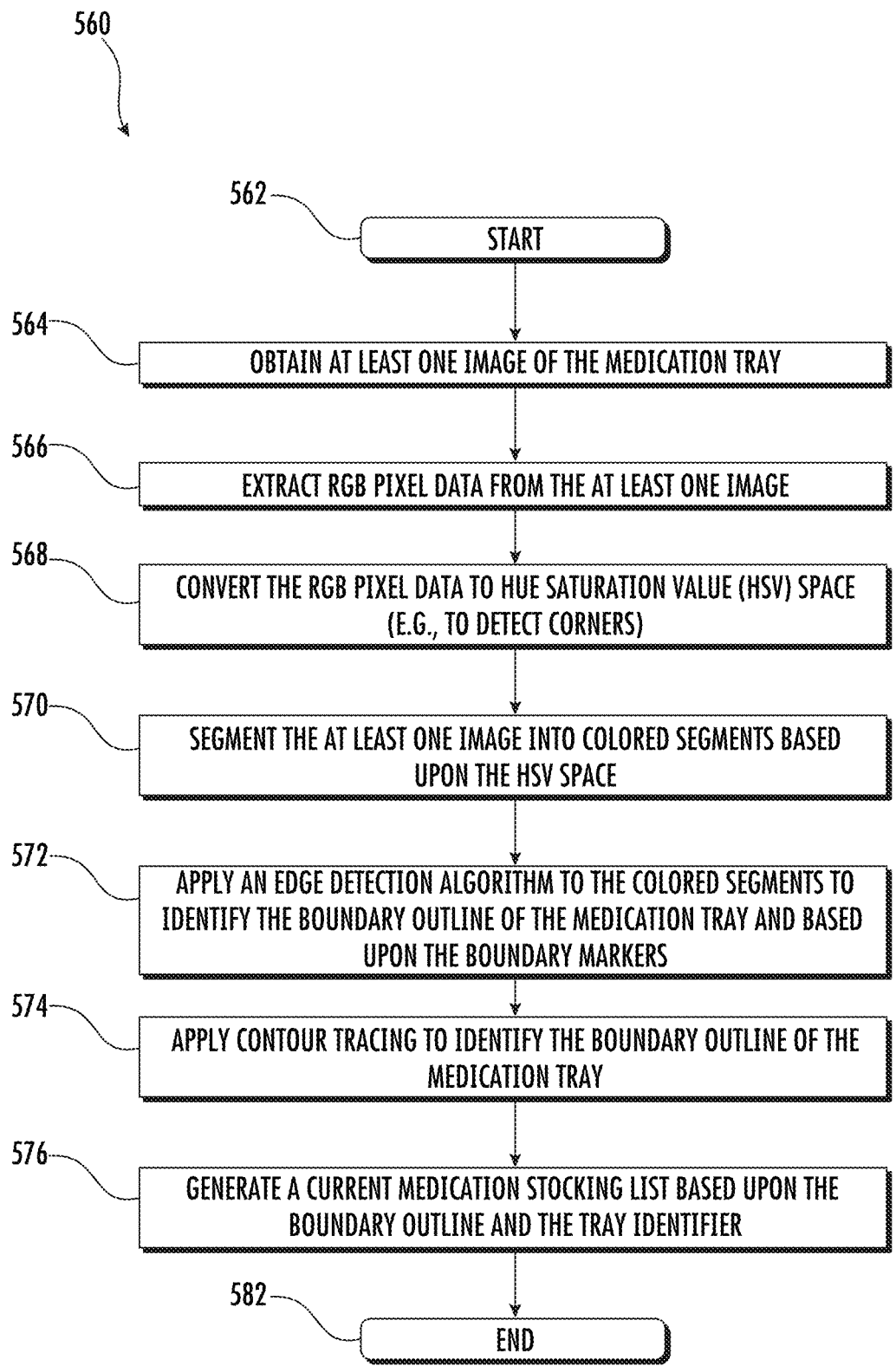
FIG. 32 is a flow diagram illustrating operation of the mobile wireless communications device of FIG. 23.

Referring now to FIGS. 23-31 and the flowchart 560 in FIG. 32, beginning at Block 562 more detailed operations of the mobile wireless communications device 440 with respect to the medication inventory system 420 will now be described. At Block 564, the mobile wireless communications device 440 obtains at least one image 447 of the medication tray 430.

Figure 25:
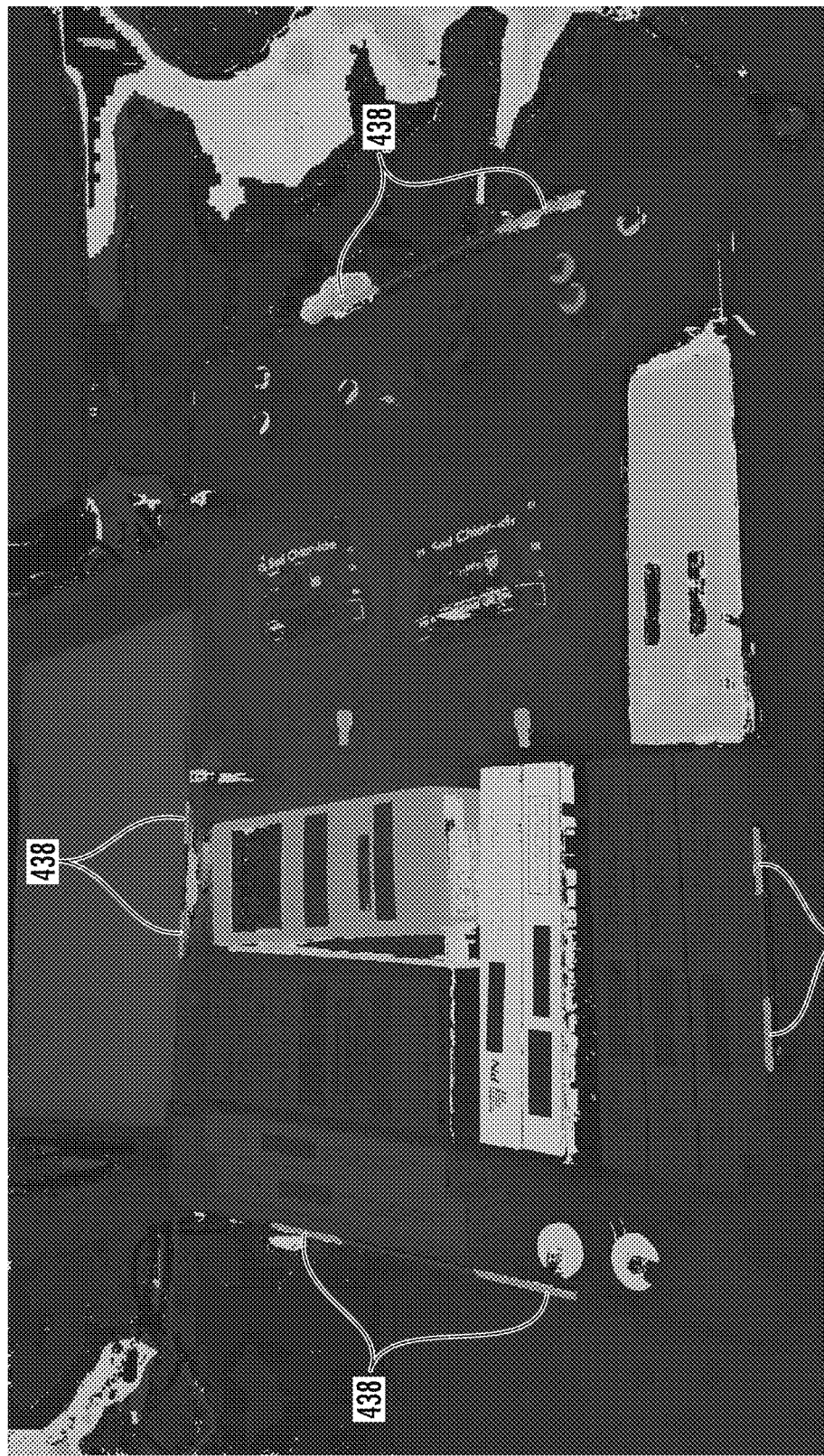
FIG. 25 is an exemplary image of a medication tray with image data converted to hue saturation value (HSV) space according to an embodiment.

The mobile wireless communications device 440 extracts red, green, and blue (RGB) pixel data 457 from the at least one image 447 (Block 566). At Block 568, the RGB pixel data 457 is converted to hue saturation value (HSV) space. In other words, as will be appreciated by those skilled in the art, to detect the corners, the RGB pixel data 457 from the camera 444 is converted to HSV space to yield HSV converted RGB pixel data 458. In the hue channel, the value of each pixel corresponds to the color of the pixel (FIG. 25).

Figure 26:
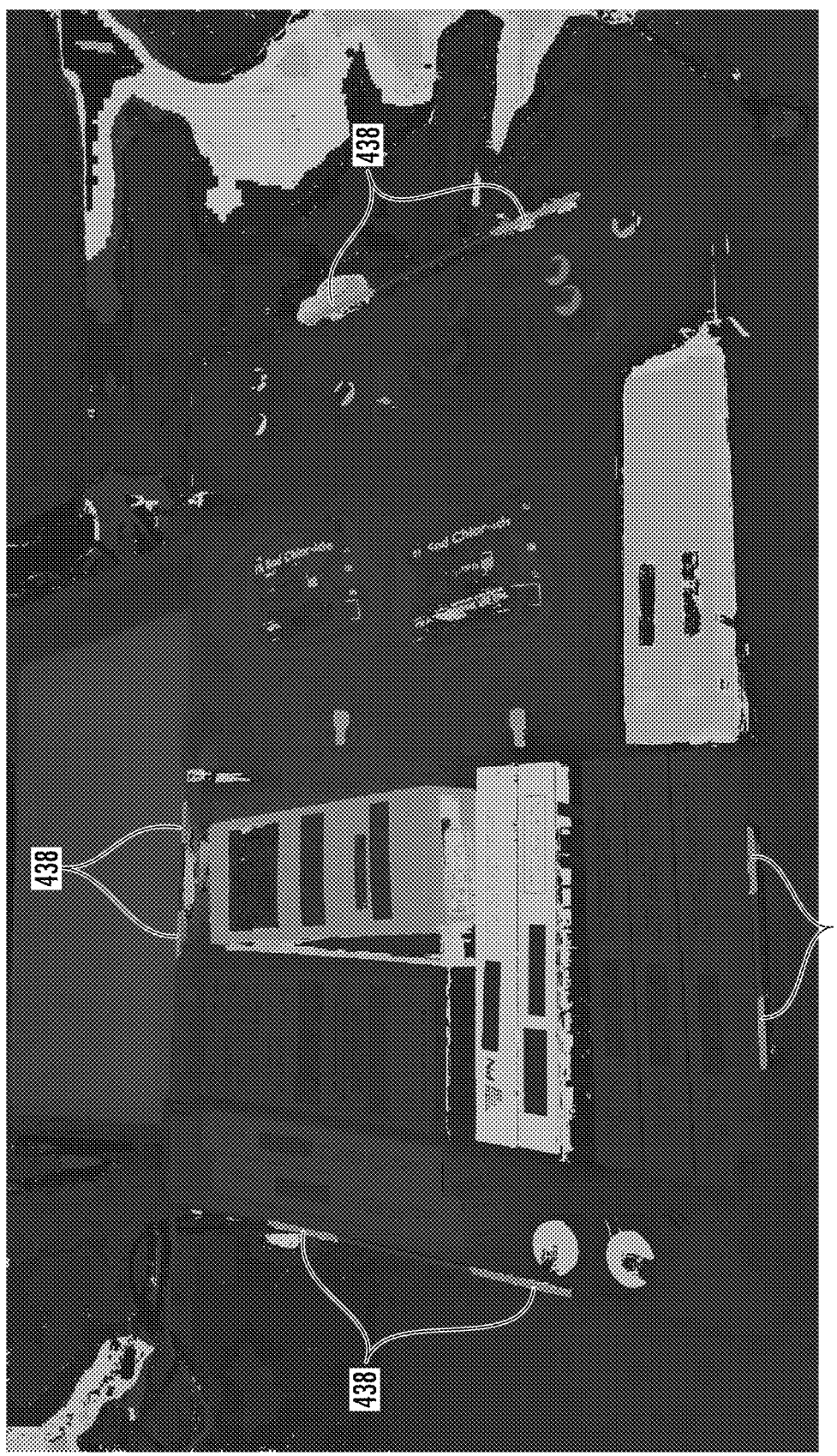
FIG. 26 is an exemplary image of a medication tray with the HSV converted image data segmented into the color yellow according to an embodiment.
Figure 27:
FIG. 27 is an exemplary image of a medication tray with the HSV converted image data segmented into the color teal according to an embodiment.
Figure 28:
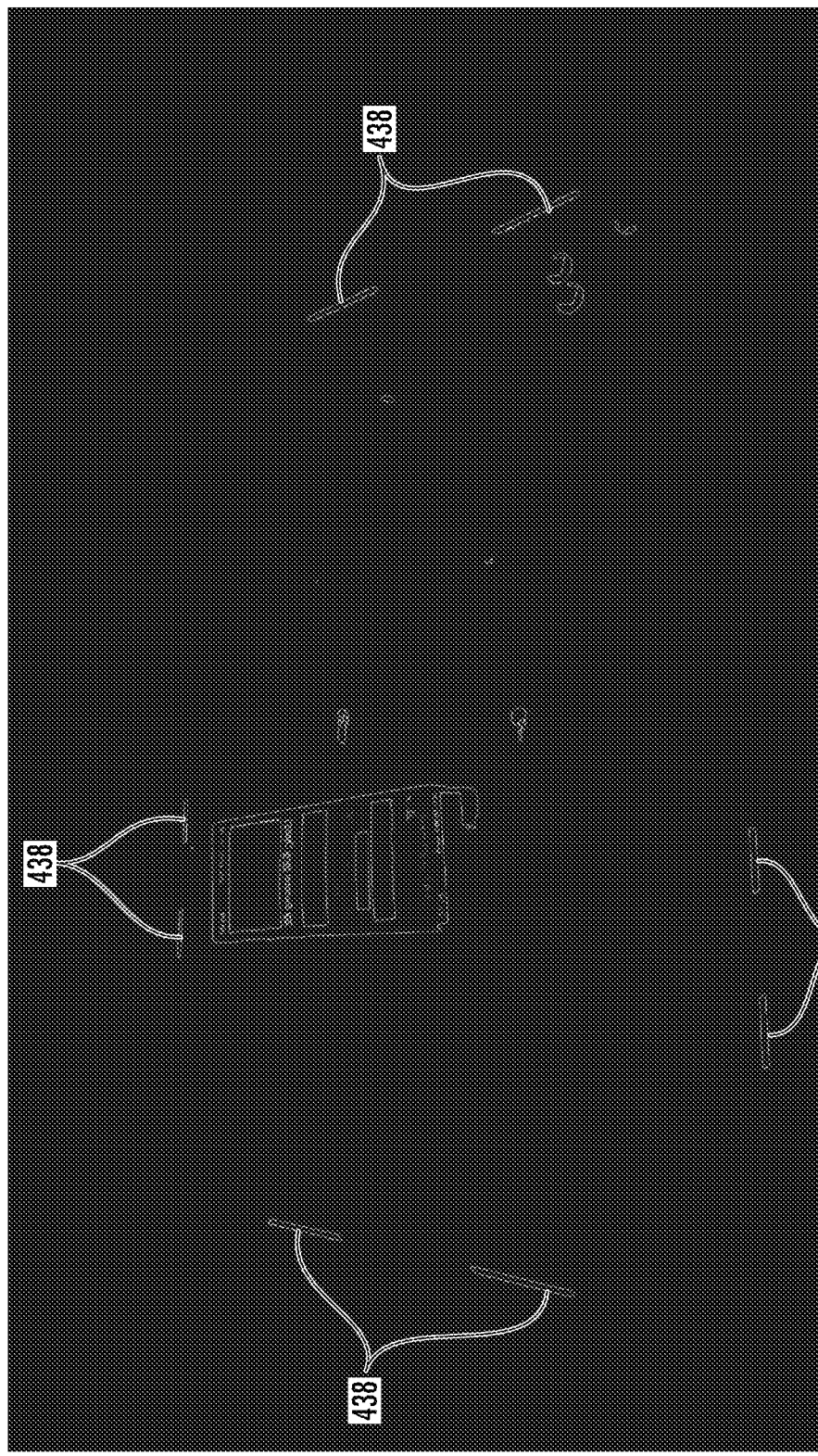
FIG. 28 is the exemplary image of the medication tray of FIG. 27 with the Canny edge detection technique applied according to an embodiment.
Figure 29:
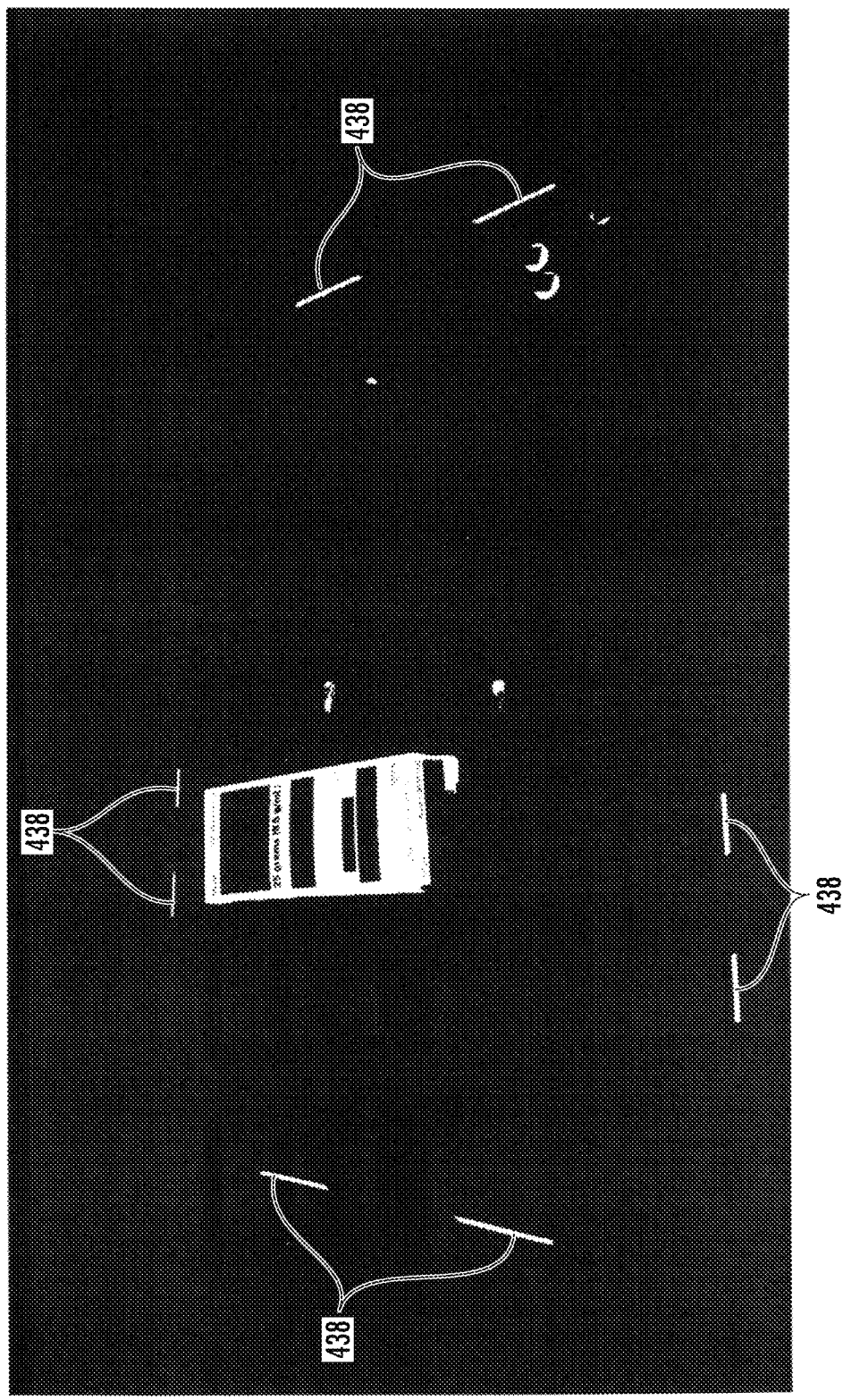
FIG. 29 is the exemplary image of the medication tray of FIG. 26 with the Canny edge detection technique applied according to an embodiment.

The at least one image is segmented 459, at Block 570, based upon the HSV space. More particularly, the HSV space is used to segment the at least one image 447 into "blobs" of the appropriate color (e.g., teal and yellow; FIGS. 26 and 27, respectively). Edge detection techniques or an edge detection algorithm 455 are applied to the color segments 459 to identify the boundary outline 456 of the medication tray 430 (Block 572). More particularly, the edge detection algorithm 455 may be applied to detect the edges of the "blobs." As will be appreciated by those skilled in the art, edge detection algorithms may include the Canny, Sobel, or Laplacian of Gaussian techniques. Referring briefly to FIGS. 28 and 29, application of the Canny algorithm to images in FIGS. 26 and 27, respectively are illustrated. Other and/or additional techniques may be used for edge detection.

At Block 574, the mobile wireless communications device 440, via the controller 445, applies contour tracing. These contours may be filtered so that the contours that can represent the boundary markers 438, and more particularly, the colored machine readable indicia 453. The filtering may be based on a perimeter length of the medication tray 430, aspect, and an assumption about a ratio of the length of the machine readable indicia 453 to the overall size of the medication tray. A smallest rectangle that includes the contour of each "blob" is then computed.

Figure 18:
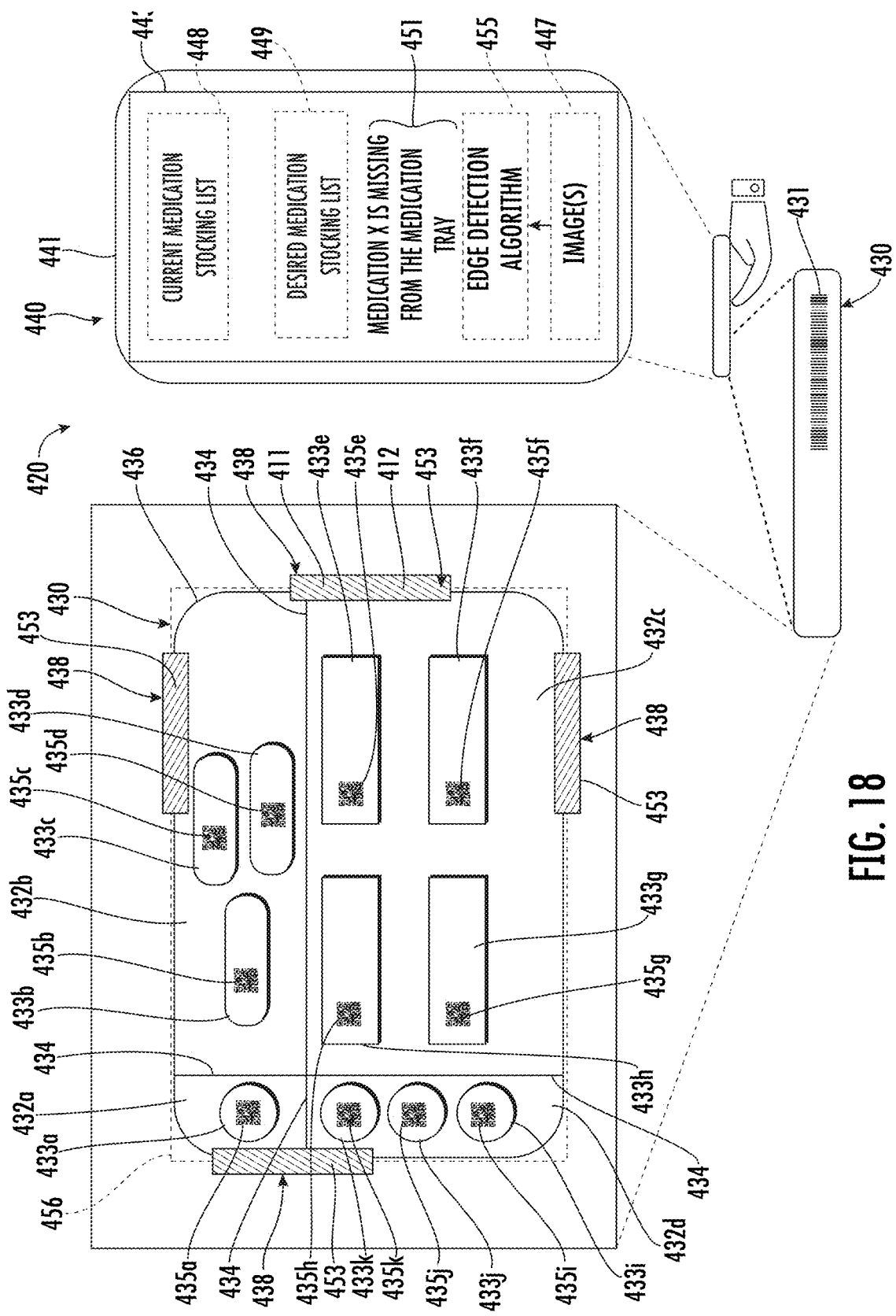
FIG. 18 is a schematic diagram of a medication inventory system in accordance with another embodiment.
Figure 19:
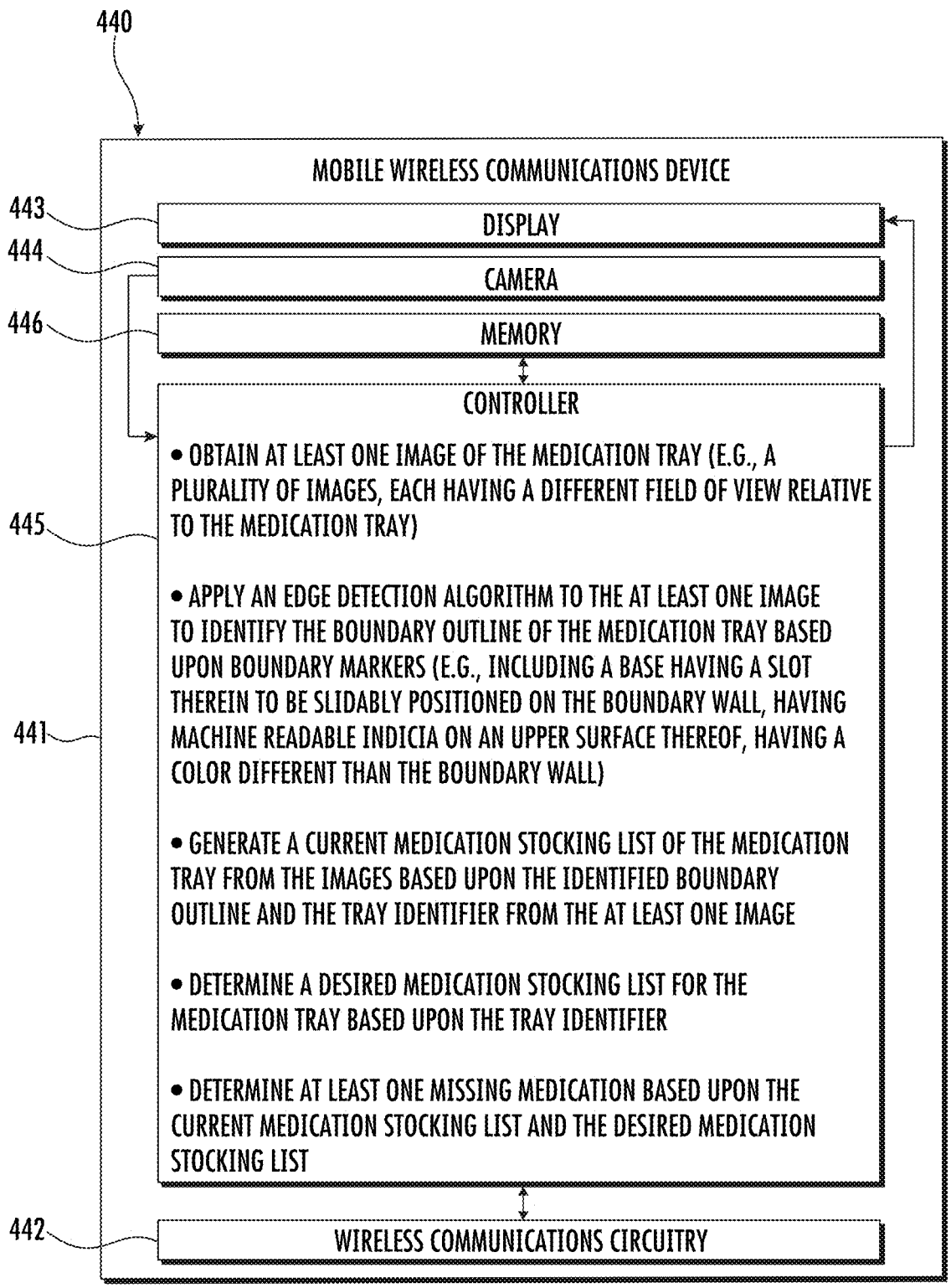
FIG. 19 is a schematic block diagram of the mobile wireless communications device of FIG. 18.
Figure 20:
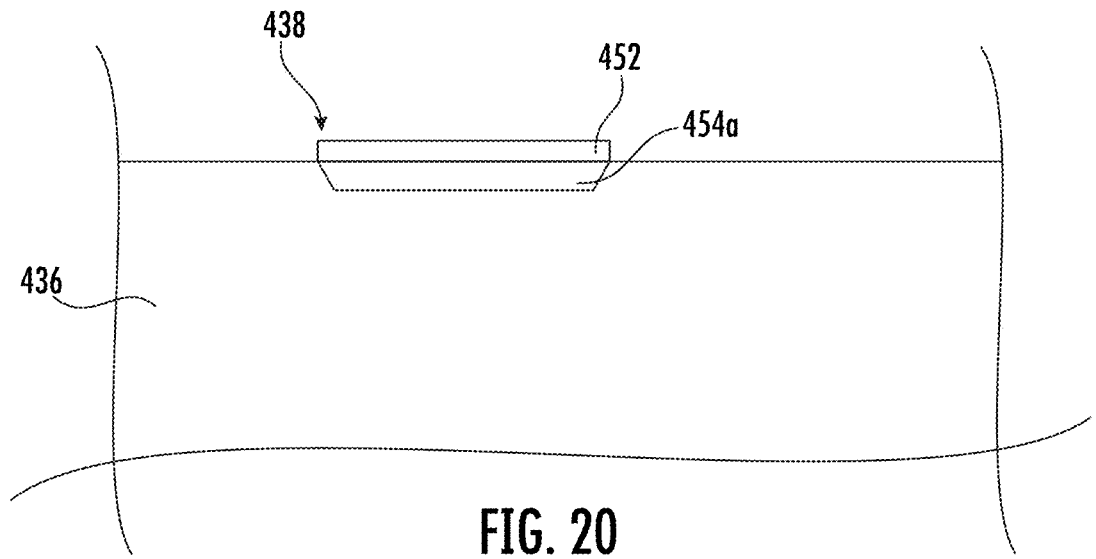
FIG. 20 is a schematic side view of a boundary marker in accordance with an embodiment.
Figure 21:
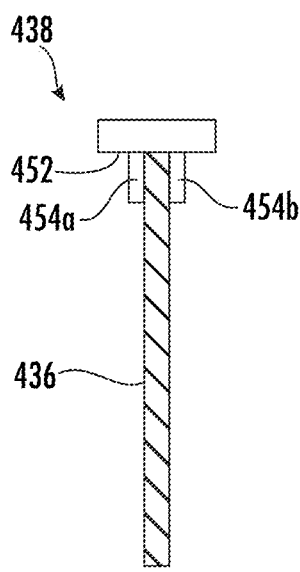
FIG. 21 is a schematic side view of a boundary marker in accordance with an embodiment.

Each machine readable indicia 453 or adhesive label may include relatively bright or vibrant colors, for example, that may be printed with a CMYK printing process. Each machine readable indicia 453 may further include first and second color segments 411, 412 (FIGS. 18 and 30). An angle may be between the first and second color segments 411, 412, for example, so that the first and second color segments 411, 412 overlap. By overlapping the first and second segments 411, 412, a smallest enclosing rectangle of each segment may thus overlap with its neighbor, as will be appreciated by those skilled in the art. Colors may be chosen to include a relatively wide black border so that segmented color blobs do not merge into any neighboring regions with similar colors. This may allow for a wide range of hues, saturations, and values to be included in the detected color segments, for example, yellow 411 and teal, 412. (FIG. 30).

With respect to yellow and teal (i.e., yellow and teal "blobs"), for each yellow rectangle any coincident teal rectangles are found. If any yellow rectangle has two or more bounding teal rectangles, the subset of one yellow and two teal rectangles that is closest to having their centers in a line is added to a list of candidate edges.

Any yellow rectangles that are bounded by only one teal rectangle are added to a list of secondary candidates, on the assumption that some teal rectangles may not be well detected. If the total number of primary candidate edges is less than four, then these secondary candidates are added to the primary candidates in combinations totaling exactly four candidates, until the first set of candidate edges found intersect within the boundaries of the overall image. If the total number of primary candidate edges is greater than four, or no set of four primary and secondary candidate edges is found that intersect within the image 447, then the image is rejected and the user may be directed to take the picture of the medication tray 430 from a different angle or with better lighting, for example.

For the final list of candidate edges, edge direction is detected by drawing a line between the center of the two bordering teal rectangles, or in the case of a yellow region with only one teal region bordering, drawing a line from the center of the yellow region to the center of the teal region. The corners are then computed by extending the lines of each edge and searching for intersection with other line edges. Referring briefly to FIG. 31, a visualization of the operations described herein illustrates that magenta rectangles 413 represent yellow regions 414, green rectangles 415 represent coincident teal regions 417, lines from the green center to the green center are the detected edge line segments, and the red circles 416 are the detected corners.

Further refinement may be performed, for example, in the case where more than four candidates are found (either primary or combination of primary and secondary). The further refinement may include computing the set of corners for each potential set of four candidate edges, and using the set of corners closest to a rectangular area as the overall result.

While yellow and teal have been described herein with respect to the colors of the machine readable indicia 453, those skilled in the art will appreciate that other colors may be used. Additionally, where the medication tray 430 is sized so that each boundary marker 438 does not slidably position on the boundary wall 436, additional boundary marker and indicia templates may be used and may include a relatively flat upper surface that may point true at the corners coincident to the edge. With respect to drawers or cabinets, for example, the indicia 453 may be sized to be smaller than those used with the medication tray 430, and the boundary markers 438 may be applied to a visible inside wall, with the color region as close to the top of the wall as possible. In order to be visible to the mobile wireless communications device 440, the indicia 453 may be applied to the outside rather than the inside of the drawer. At Block 576, the mobile wireless communications device 440 generates a current medication stocking list 448 of the medication tray 430 based upon the identified boundary outline 456 and the tray identifier 431 from the one or more images 447. Operations end at Block 582.

While operations have been described with respect to one image, the mobile wireless communications device 440 may obtain more than one image 447, which may be at different fields of view relative to the medication tray 430. In the case where multiple images 447 are obtained, the mobile wireless communications device 440 may determine the boundary outline 456 based upon the different fields of view relative to the medication tray 430, for example, using techniques described above with respect to the embodiments illustrated in FIGS. 4-7. Moreover, the mobile wireless communications device 440 may apply the edge detection algorithm 455 and operations described above to each image and aggregate, combine, average, or interpolate the determined boundary outlines to determine a final boundary outline 456.

As will be appreciated by those skilled in the art, the medication inventory system 420 advantageously detects the boundary outline 456 or extent of the medication tray 430 in different operating conditions. This is in contrast to approaches where operations are dependent on the image obtained being aligned and held, for example, by a user directly above a center of a medication tray. The medication inventory system 420 also may decrease processing times by not having to process portions of an image or images outside of the boundary outline 456.

Additionally, the segmentation and/or inclusion of identification of corners, as described herein may be particularly helpful for addressing the non-linear nature of camera lenses, existing long vertical and horizontal features both in the medication tray itself as well as the surrounding environment, and imprecise edge detection, for example. Moreover, the medication inventory system 420 addresses shortcoming in other approaches, such as, for example, contour tracing, which detects edge with imprecision (pixels that are part of the edge not being detected), and contours both external and internal to the medication tray 430 are detected as part of the tray edge or the boundary outline 456 of the medication tray.

Indeed, the medication inventory system 420 described herein may provide a robust technique to address a variety of distortions and imperfections as well as occlusion of the boundary outline 456 of the medication tray 430. Moreover, the color segmentation techniques may be considered reliable in a variety of lighting conditions and are relatively immune to glare and shadow. By using a strong signal to represent the edge, the edge detection algorithm can search through potential candidates to find one which meets a fairly stringent set of geometric criteria, reducing the chance of false positives while also providing additional secondary candidates that may be when no perfect boundary outline match is determined, for example. Thus, the system described herein may be moderately robust but still capable of rejecting inputs that grossly mismatch the expected criteria.

Still further, when experiments were conducted using other approaches to edge detection, insufficient results were generated. For example, for Hough feature detection, the non-linear nature of camera lenses, existing long vertical and horizontal features, both in the medication tray itself as well as the surrounding environment, and imprecise edge detection caused less than desirable results. Further details of a medication inventory system that uses a Hough algorithm can be found in U.S. application Ser. No. 17/162,781, assigned to the present assignee, and the entire contents of which are hereby incorporated by reference. Contour tracing likewise produced results that were undesirable due to imprecise edge detection (pixels that are part of the edge not being detected), and contours, both external and internal to the tray, being detected as part of the tray edge.

Still further, a segmented Hough approach, while addressing some of the deficiencies set forth above, relies on a-priori knowledge of the approximate size of the medication tray 430 and successful decoding of the tray identifier 431 to identify the boundary outline 456 of the medication tray. The present embodiments of the medication inventory system 420 do not rely on a-priori knowledge of the medication tray 430 and/or tray identifier 431 to identify the boundary outline 456 of the medication tray.

A method aspect is directed to a method of processing medication inventory in a medication inventory system 420 that includes a medication tray 430 that includes a plurality of compartments 432a-432n for storing respective medications 433a-433k. The medication tray 430 also includes a boundary wall 436 defining a boundary outline 456 of the medication tray, and the medication tray has a tray identifier 431 associated therewith. The method includes using a mobile wireless communications device 440 to obtain at least one image 447 of the medication tray 430, and apply an edge detection algorithm 455 to the at least one image to identify the boundary outline 456 of the medication tray based upon a plurality of boundary markers 438 carried by the boundary wall. The method also includes using the mobile wireless communications device 440 to generate a current medication stocking list 448 of the medication tray 430 based upon the identified boundary outline 456 and the tray identifier 431 from the at least one image 447.

A computer readable medium aspect is directed to a non-transitory computer readable medium for a medication inventory system 420 that includes a medication tray 430 including a plurality of compartments 432a-432n for storing respective medications 433a-433k. The medication tray 430 includes a boundary wall 436 defining a boundary outline 456 of the medication tray, and the medication tray has a tray identifier 431 associated therewith. The non-transitory computer readable medium includes computer executable instructions that when executed by a controller 445 of a mobile wireless communications device 440 cause the controller to perform operations. The operations include obtaining at least one image 447 of the medication tray 430, and applying an edge detection algorithm 455 to the at least one image to identify the boundary outline 456 of the medication tray based upon a plurality of boundary markers 438 carried by the boundary wall 436. The operations also include generating a current medication stocking list 448 of the medication tray 430 based upon the identified boundary outline 456 and the tray identifier 431 from the at least one image 447.

Figure 33:
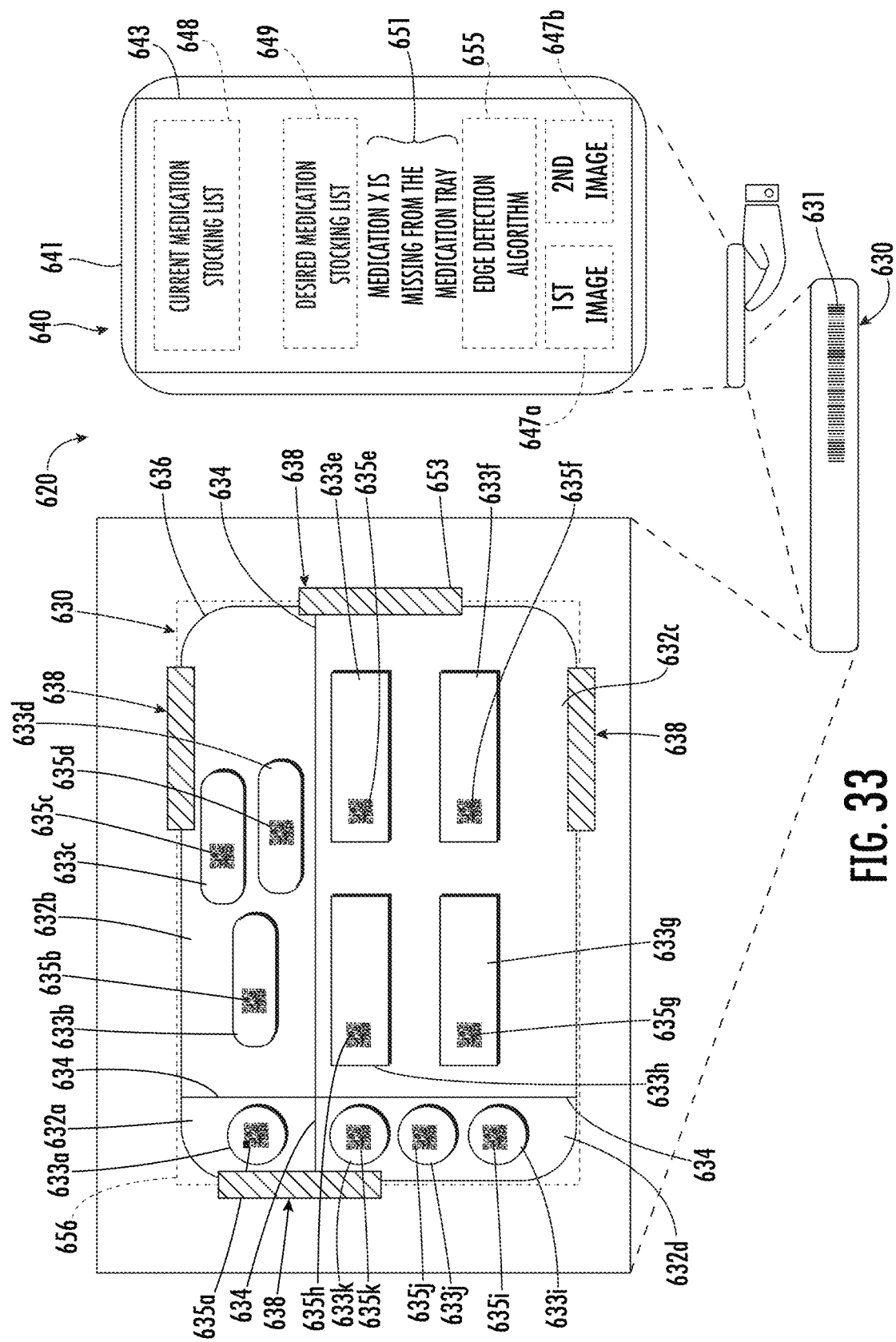
FIG. 33 is a schematic diagram of a medication inventory system in accordance with another embodiment.
Figure 34:
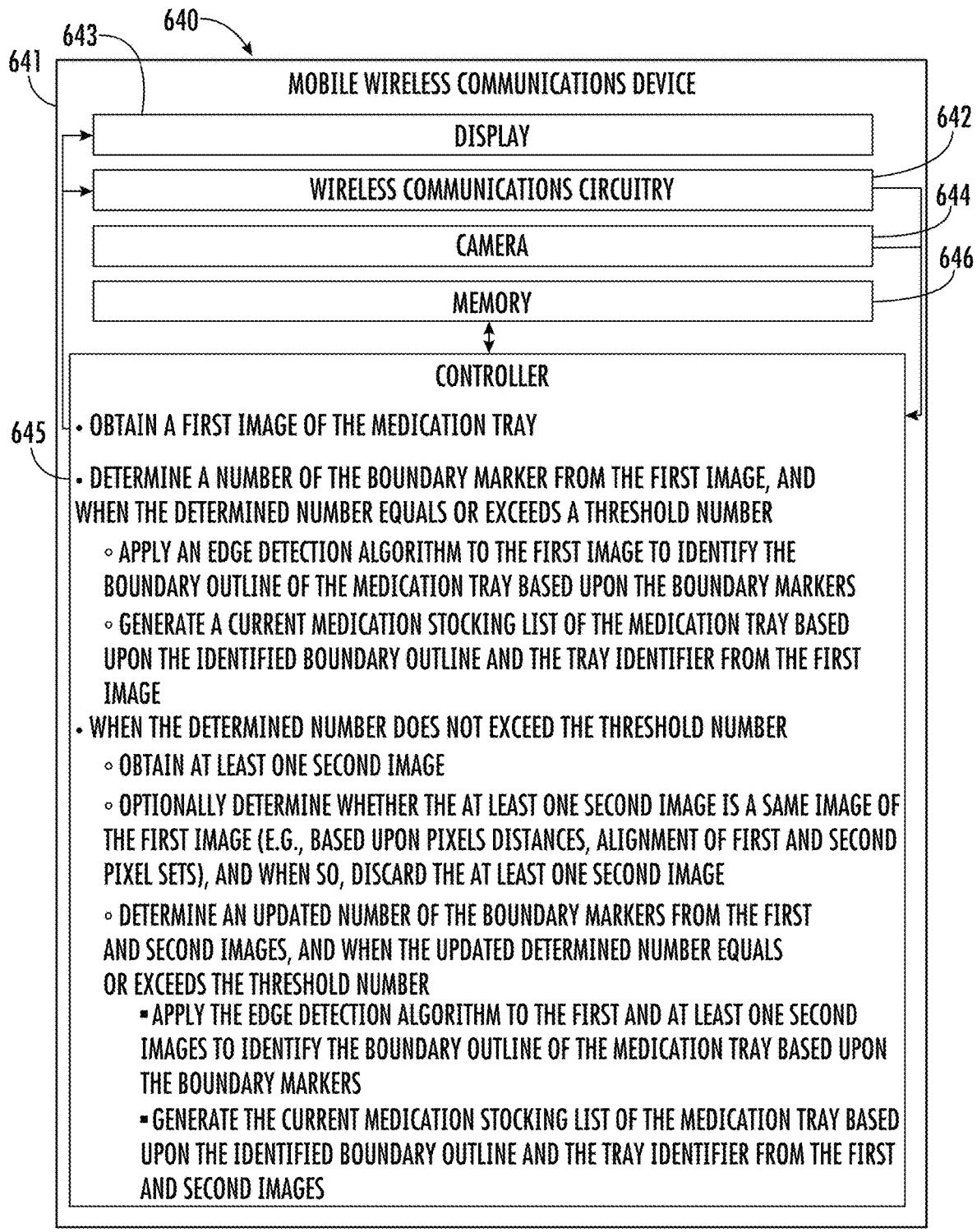
FIG. 34 is a schematic block diagram of the mobile wireless communications device of FIG. 33.

Referring now to FIGS. 33-34, in another embodiment, a medication inventory system 620 includes a medication tray 630 that includes compartments 632a-632k, defined by partitions 634, for storing respective medications 633a-633k. Similar to the embodiments described above, each compartment may store a medication 633a-633k, multiple medications, a medical or medicated device, a medication container that includes individual medications therein, or other item or substance used for medical treatment. For example, the medication tray 630 may be part of a crash cart, as will be appreciated by those skilled in the art. Of course, the medication tray 630 may be used in other medical environments, for example, an examination room, emergency room, treatment room, operating room, etc. For example, the medication tray 630 may be in the form of a drawer within a medication cabinet or medication dispensing cabinet. Each medication 633a-633k has a respective medication identifier 635a-635k associated therewith, for example, a barcode, quick-response (QR) code, alphanumeric characters, or other optically recognizable and unique code.

The medication tray 630 includes a boundary wall 636 that defines a boundary outline 656 of the medication tray. More particularly, the boundary wall 636 includes first and second opposing perimeter walls that define the boundary outline. In some embodiments, for example, where the medication tray 630 has a round shape, there may be only a single boundary wall 636.

The medication inventory system 620 also includes boundary markers 638 that are illustratively carried by the boundary wall 636. Each boundary marker 638 is similar to the boundary markers described above, for example, with respect to embodiments corresponding to FIGS. 18-21.

Also, similarly to the above-described embodiments, the medication tray 630 has a tray identifier 631 associated therewith. The tray identifier 631 may be in the form of a barcode, for example, that may be printed or applied (e.g., via an adhesive label) on the medication tray 630. The tray identifier 631 may be in the form of another type of identifier, for example, QR code, alphanumeric characters, or other optically recognizable and unique code.

The medication inventory system 620 also includes a mobile wireless communications device 640, illustratively in the form of a smartphone. The mobile wireless communications device 640 illustratively includes a housing 641 and wireless communications circuitry 642 carried by the housing. The mobile wireless communications device 640 also includes a display 643, for example, a touch display, carried by the housing 641. A controller 645 is coupled to the wireless communications circuitry 642 and the display 643. A camera 644 is also carried by the housing 641 and coupled to the controller 645. One or more input devices may be carried by the housing 641 and coupled to the controller 645. While the mobile wireless communications device 640 is illustratively in the form of a smartphone, the mobile wireless communications device may be in the form of a tablet, laptop computer, or wearable device, for example.

Figure 35:
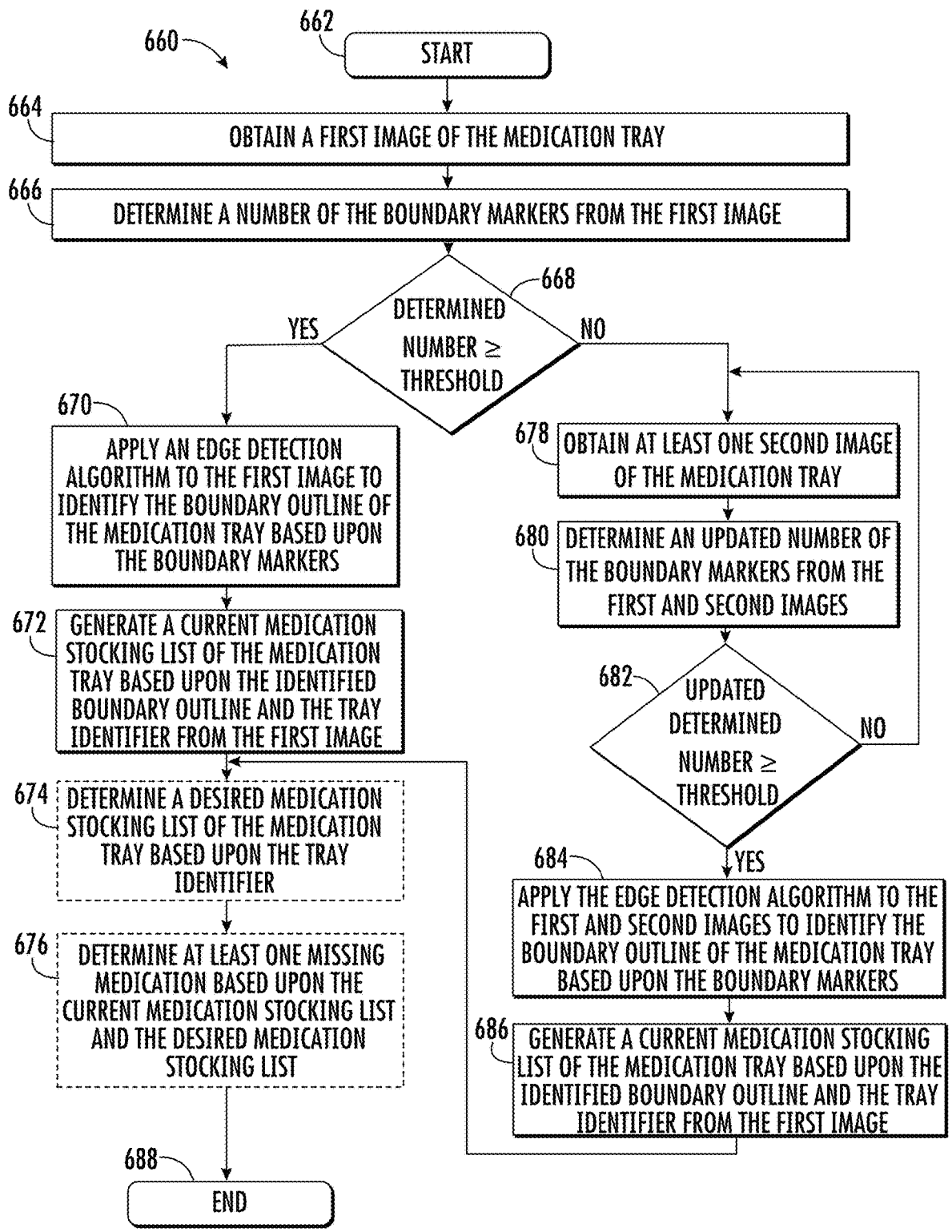
FIG. 35 is a flow diagram illustrating operation of the mobile wireless communications device of FIG. 33.

Referring now additionally to the flowchart 660 in FIG. 35, beginning at Block 662, operations of the mobile wireless communications device 640 of the medication inventory system 620 will now be described. While operations of the mobile wireless communications device 640 are described, it will be appreciated by those skilled in the art that the controller 645 and an associated memory 646 cooperate to perform the operations.

At Block 664 the mobile wireless communications device 640 obtains a first image 647a of the medication tray 630, for example, via the camera 644 carried by the housing 641 of the mobile wireless communications device 640. At Block 666, the mobile wireless communications device 640 determines a number of the boundary markers 638 from the first image 647a. When the determined number of boundary markers 638 from the first image 647a exceeds a threshold number (Block 668), the mobile wireless communications device applies an edge detection algorithm 655 to the first image 647a to identify the boundary outline 656 of the medication tray 630 based upon the boundary markers 638 (Block 670).

As will be appreciated by those skilled in the art, the obtained first image 647a may be of insufficient quality to accurately determine the boundary markers 638, and thus less accurately determine the boundary outline 656. By determining the number of boundary markers 638 from the first image and comparing the number to a threshold number, the mobile wireless communications device 640 advantageously may not permit a less accurate boundary outline 656 determination by permitting the boundary outline determination after the determined number of boundary markers 638 equals or exceeds the threshold number, for example. For example, the threshold number may be four, representing four edges of a medication tray 630, so that if only three boundary markers are determined, and thus only three edges of the medication tray, the mobile wireless communications device 630 does not perform the edge detection, and thus does not generate a current medication stocking list.

At Block 672, when the determined number boundary markers 638 exceeds the threshold, the mobile wireless communications device 640 generates a current medication stocking list 648 of the medication tray 630 based upon the identified boundary outline 656 and the tray identifier 631 from the first image 647a. More particularly, the mobile wireless communications device 640 generates the current medication stocking list 648 similarly to the operations described above, but also generates the current medication stocking list based upon the boundary outline 656. Those skilled in the art will appreciate that by basing the current medication stocking list based upon the boundary outline 656, a more accurate and quicker processing time to generate the current medication stocking list 648 may be obtained since the controller 645 may not process parts of the image outside the boundary outline 656.

The mobile wireless communications device 640 may, when the determined number boundary markers 638 exceeds the threshold, determine a desired medication stocking list 649 of the medication tray 630 based upon the tray identifier 631 (Block 674), for example, using techniques along the lines described above. The mobile wireless communications device 640 may also, at Block 676, determine one or more missing medications (e.g., that may have been used) based upon the current medication stocking list 648 and the desired medication stocking list 649, for example, to generate a notification 651 and using the techniques and similar to the embodiments described above.

In some embodiments, when the determined number boundary markers 638 exceeds the threshold, the mobile wireless communications device 640 may also determine expired medications or nearly expired medications within the medication tray 630 based upon the medication identifiers 635a-635k. The operations of the mobile wireless communications device 640 with respect to determining expired medications are described above.

When, at Block 668, the determined number does not exceed the threshold number (e.g., only three edges detected when the threshold number is four), the mobile wireless communications device 640 obtains a second image 647b of the medication tray 630 (Block 678). The second image 647b may be obtained from the camera 644 of the mobile wireless communications device 640, for example, based upon a prompt on the display to a given user to obtain another image.

At Block 680, the mobile wireless communications device determines an updated number of boundary markers 638 from the first and second images 647a, 647b. When, at Block 682, the updated determined number of boundary markers 638 equals or exceeds the threshold number, the mobile wireless communications device 640 applies the edge detection algorithm to the first and second images to identify the boundary outline 656 of the medication tray 630 based upon the boundary markers 638 (Block 684), and generates the current medication list 648 based upon the identified boundary outline 656 and the tray identifier 631 from the first and second images 647a, 647b (Block 686). The first and second images 647a, 647b may be combined, for example, by way of pixel averaging.

More particularly, conceptually, for example, the mobile wireless communications device 640 detects when the same boundary is in two or more images and counts the same boundary outline once. Pixel locations, for example, across detections or obtained images are averaged to more accurately measure the boundary outline, and updated measurements are related first to the pixel coordinate space of the first image, and then once all boundaries, e.g., four, are detected, to all other measures previously taken to an absolute real world coordinate space describing the actual tray. In other words, the concept described in the present embodiments of, "first measuring in one arbitrary coordinate system, then measuring in a real coordinate system" is a significant change to previous recognition techniques.

In some embodiments, the mobile wireless communications device 640, before determining the number of boundary markers 638 from the second image, or any subsequent obtained image, may determine whether the second or subsequent image is the same as or is a duplicate to the first image or previous image. To determine whether images are duplicates, the mobile wireless communications device 640 may determine a pixel distance between aligned images, and more particularly, the pixel sets representing the images being compared. For example, if two images align to within 30-pixels (e.g., align at the borders), the mobile wireless communications device 640 may determine that the images are duplicates. If an image is a duplicate, the mobile wireless communications device 640 may disregard or discard the duplicate image. Those skilled in the art will appreciate that the duplicate image generally will not add detection of a boundary marker 638 if the boundary marker was not detected in the previous image. Thus, to process the duplicate image to apply edge detection, for example, would increase processing time.

More than one second image 647b may be obtained. For example, if it is determined that the combination of the first and second images 647a, 647b does not yield a determination of the number of boundary markers 638 that exceeds the threshold (Block 682). Additional or more detailed operations of the mobile wireless communications device 640, for example, pixel data processing, contour tracing, corner identification, may be performed, and are similar to the operations and techniques described above.

Similarly, when the updated determined threshold number equals or exceeds the threshold number, the mobile wireless communications device 640 may optionally, as described above, determine the desired medication stocking list (Block 674) and/or determine the at least one missing medication (Block 676). Operations end at Block 688.

A method aspect is directed to a method of processing medication inventory in a medication inventory system that includes a medication tray 630 that includes a plurality of compartments for storing respective medications. The medication tray 630 also includes a boundary wall defining a boundary outline 656 of the medication tray 630, and the medication tray 630 may have a tray identifier 631 associated therewith. The method includes using a mobile wireless communications device 640 to obtain a first image 647a of the medication tray 630, and determine a number of the plurality of boundary markers 638 from the first image 647a. When the determined number equals or exceeds a threshold number, the method includes using the mobile wireless communications device 640 to apply an edge detection algorithm to the first image 647a to identify the boundary outline 656 of the medication tray 630 based upon a plurality of boundary markers 638, and generate a current medication stocking list 648 of the medication tray 630 based upon the identified boundary outline 656 and the tray identifier 631 from the first image 647a. The method also includes using the mobile wireless communications device 640 to, when the determined number does not exceed the threshold number, obtain at least one second image 647b of the medication tray 630, and determine an updated number of the plurality of boundary markers 638 from the first and at least one second image. When the updated determined number equals or exceeds the threshold number, the method includes using the mobile wireless communications device 640 to apply the edge detection algorithm to the first and at least one second images to identify the boundary outline 656 of the medication tray 630 based upon the plurality of boundary markers 638, and generate the current medication stocking list 648 of the medication tray 630 based upon the identified boundary outline 656 and the tray identifier 631 from the first and at least one second images.

A computer readable medium aspect is directed to a non-transitory computer readable medium for a medication inventory system that includes a medication tray 630 including a plurality of compartments for storing respective medications. The medication tray 630 includes a boundary wall defining a boundary outline 656 of the medication tray 630, and the medication tray 630 has a tray identifier 631 associated therewith. The non-transitory computer readable medium includes computer executable instructions that when executed by a controller 645 of a mobile wireless communications device 640 cause the controller 645 to perform operations. The operations include obtaining a first image 647a of the medication tray 630, and determining a number of the plurality of boundary markers 638 from the first image 647a. The operations also include, when the determined number equals or exceeds a threshold number, applying an edge detection algorithm to the first image 647a to identify the boundary outline 656 of the medication tray 630 based upon the plurality of boundary markers 638, and generating a current medication stocking list 648 of the medication tray 630 based upon the identified boundary outline 656 and the tray identifier 631 from the first image 647a. The operations also include, when the determined number does not exceed the threshold number, obtaining at least one second image 647b of the medication tray 630, and determining an updated number of the plurality of boundary markers 638 from the first and the at least one second images. The operations further include, when the updated determined number equals or exceeds the threshold number, applying the edge detection algorithm to the first and at least one second images to identify the boundary outline 656 of the medication tray 630 based upon the plurality of boundary markers 638, and generating the current medication stocking list 648 of the medication tray 630 based upon the identified boundary outline 656 and the tray identifier 631 from the first and at least one second images.

In another embodiment, boundary outline identification of a medication tray may be performed via a server. The server, which includes a processor cooperating with a memory executes an algorithm that, by way of the algorithm, detects borders or boundaries outside detected items (e.g., medications) as the tray borders or the boundary outline. Further details of the algorithm will now be described, for example, as performed by the processor.

Canny detection may be used to detect lines in the original obtained image. An area that corresponds to the detected items is masked out of the resulting detection. The top longest lines, for example, the top longest 1500 lines, are considered. Smaller lines that are roughly co-linear may be combined into larger lines, for example, so long as the new line is within a threshold, for example, a degree or two, of pointing in the same direction, and has at least 30% of its length accounted for by the previous lines, and the new line does not go within the borders of the detected barcodes.

Line combining is performed in successive stages, with each succeeding stage allowing more variation in the input than the previous stage. When done, the lines are sorted for length and the top longest lines, for example, the top longest 16 longest lines are considered as candidates for the borders of or the boundary outline of the medication tray, in order of length. Each unique set of candidate borders are connected into a quadrilateral. That quadrilateral is tested to determine whether the angles are within a threshold amount of degrees of square, for example, 30-degrees. A determination is also made as to whether the quadrilateral is convex (e.g., does not intersect itself), and whether the quadrilateral fully or nearly fully includes the detected items. Based thereon, the candidate border is scored. The score assigned is based upon the amount of overlapping pixels. For example, the score may be determined to be 10,000 plus the number of border pixels (e.g., any) that nearly overlap (<1 px) candidate borders by applying the square root of the area of the detected border. These operations select borders that may be considered to be a well fit to the candidate lines—even nearby but not quite co-linear lines—and also comprise a relatively small, for example, the smallest, space that includes the identifiers (e.g., barcodes) detected. The highest scoring candidate border is returned as the boundary outline the medication tray.

In other words, more simply, the algorithm, identifies barcodes or identifiers, and applies edge detection, for example, as described above. Any lines with a boundary area, particularly edges, inside the medication tray boundary are filtered. Text may be used to aid in determining tray boundaries. The longest lines (e.g., 500-1500), are obtained and combined, with the combination occurring successively to increase compliance with iteration. Any lines that are representative of a barcode are filtered out, and the lines are analyzed to determine whether the lines are nearly co-linear as one long line. A quadrilateral is "drawn" based upon intersecting lines. A score is generated based upon the number of pixels that intersect edges. While the present embodiments do not use boundary markers, those skilled in the art will appreciate that may be used for further accuracy.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication inventory system comprising:
   a medication tray comprising a plurality of compartments for storing respective medications, the medication tray comprising a boundary wall defining a boundary outline of the medication tray, and the medication tray having a tray identifier associated therewith for identifying a desired medication stocking list of desired medications within the medication tray;
   a plurality of boundary markers carried by the boundary wall of the medication tray; and
   a mobile wireless communications device configured to obtain a first image of the medication tray,
      determine a number of the plurality of boundary markers from the first image, and when the determined number equals or exceeds a threshold number
         apply an edge detection algorithm to the first image to identify the boundary outline of the medication tray based upon the plurality of boundary markers, and
         generate a current medication stocking list of the medication tray based upon the identified boundary outline and the tray identifier from the first image, and
      when the determined number does not exceed the threshold number,
         obtain at least one second image of the medication tray,
         determine an updated number of the plurality of boundary markers from the first and the at least one second images by combining the first and at least one second images based upon determining image pixel locations in each of the first and at least one second images, mapping the pixel locations of the at least one second image to a pixel coordinate space of the first image, and mapping the pixel locations of each of the first and at least one second images to a pixel coordinate space representative of the medication tray, and when the updated determined number equals or exceeds the threshold number
            apply the edge detection algorithm to the combined first and at least one second images to identify the boundary outline of the medication tray based upon the plurality of boundary markers, and
            generate the current medication stocking list of the medication tray based upon the identified boundary outline and the tray identifier from the first and at least one second images.

2. The medication inventory system of claim 1 wherein the mobile wireless communication device is configured to, when the determined number does not exceed the threshold number, determine whether the at least one second image is a same image of the first image based upon pixel distances, and when so, discard the at least one second image.

3. The medication inventory system of claim 2 wherein the first and at least one second images each comprise respective first and at least one second pixel sets; and
   wherein the mobile wireless communications device is configured to determine whether the at least one second image is the same as the first image based upon alignment of the first and at least one second pixel sets.

4. The medication inventory system of claim 1 wherein each boundary marker comprises a body having a slot therein to be slidably positioned on the boundary wall.

5. The medication inventory system of claim 1 wherein each boundary marker has machine readable indicia on an upper surface thereof.

6. The medication inventory system of claim 1 wherein each boundary marker has a color different than the boundary wall.

7. The medication inventory system of claim 1 wherein the mobile wireless communications device is configured to:
   extract red, green, blue (RGB) pixel data from the at least one image;
   convert the RGB pixel data to hue saturation value (HSV) space;
   segment the at least one image into colored segments based upon the HSV space; and apply the edge detection algorithm to the colored segments to identify the boundary outline of the medication tray.

8. The medication inventory system of claim 1 wherein the mobile wireless communications device is configured to apply contour tracing to identify the boundary outline of the medication tray.

9. The medication inventory system of claim 1 wherein the mobile wireless communications device is configured to identify corners of the boundary outline of the medication tray based upon the edge detection algorithm.

10. The medication inventory system of claim 1 wherein the mobile wireless communications device is configured to determine the desired medication stocking list for the medication tray based upon the tray identifier.

11. The medication inventory system of claim 10 wherein the mobile wireless communications device is configured to determine at least one missing medication based upon the current medication stocking list and the desired medication stocking list.

12. A mobile wireless communications device for a medication inventory system comprising a medication tray comprising a plurality of compartments for storing respective medications, the medication tray comprising a boundary wall defining a boundary outline of the medication tray, and the medication tray having a tray identifier associated therewith for identifying a desired medication stocking list of desired medications within the medication tray, the mobile wireless communications device comprising:
a controller and an associated memory configured to
obtain a first image of the medication tray,
determine a number of a plurality of boundary markers carried by the boundary wall of the medication tray from the first image, and when the determined number equals or exceeds a threshold number
apply an edge detection algorithm to the first image to identify the boundary outline of the medication tray based upon a plurality of boundary markers, and
generate a current medication stocking list of the medication tray based upon the identified boundary outline and the tray identifier from the first image, and
when the determined number does not exceed the threshold number,
obtain at least one second image of the medication tray,
determine an updated number of the plurality of boundary markers from the first and at least one second images by combining the first and at least one second images based upon determining image pixel locations in each of the first and at least one second images, mapping the pixel locations of the at least one second image to a pixel coordinate space of the first image, and mapping the pixel locations of each of the first and at least one second images to a pixel coordinate space representative of the medication tray, and when the updated determined number equals or exceeds the threshold number
apply the edge detection algorithm to the combined first and at least one second images to identify the boundary outline of the medication tray based upon the plurality of boundary markers, and
generate the current medication stocking list of the medication tray based upon the identified boundary outline and the tray identifier from the first and at least one second images.

13. The mobile wireless communications device of claim 12 wherein the controller is configured to, when the determined number does not exceed the threshold number, determine whether the at least one second image is a same image of the first image based upon pixel distances, and when so, discard the at least one second image.

14. The mobile wireless communications device of claim 13 wherein the first and at least one second images each comprise respective first and at least one second pixel sets; and wherein the mobile wireless communications device is configured to determine whether the at least one second image is the same as the first image based upon alignment of the first and at least one second pixel sets.

15. The mobile wireless communications device of claim 12 wherein the controller is configured to:
extract red, green, blue (RGB) pixel data from the at least one image;
convert the RGB pixel data to hue saturation value (HSV) space;
segment the at least one image into colored segments based upon the HSV space; and
apply the edge detection algorithm to the colored segments to identify the boundary outline of the medication tray.

16. The mobile wireless communications device of claim 12 wherein the controller is configured to apply contour tracing to identify the boundary outline of the medication tray.

17. The mobile wireless communications device of claim 12 wherein the controller is configured to identify corners of the boundary outline of the medication tray based upon the edge detection algorithm.

18. A method of processing medication inventory in a medication inventory system comprising a medication tray comprising a plurality of compartments for storing respective medications, the medication tray comprising a boundary wall defining a boundary outline of the medication tray, and the medication tray having a tray identifier associated therewith for identifying a desired medication stocking list of desired medications within the medication tray, the method comprising:
using a mobile wireless communications device to
obtain a first image of the medication tray,
determine a number of a plurality of boundary markers carried by the boundary wall of the medication tray from the first image, and when the determined number equals or exceeds a threshold number
apply an edge detection algorithm to the first image to identify the boundary outline of the medication tray based upon a plurality of boundary markers, and
generate a current medication stocking list of the medication tray based upon the identified boundary outline and the tray identifier from the first image, and
when the determined number does not exceed the threshold number,
obtain at least one second image of the medication tray,
determine an updated number of the plurality of boundary markers from the first and at least one second images by combining the first and at least one second images based upon determining image pixel locations in each of the first and at least one second images, mapping the pixel locations of the at least one second image to a pixel coordinate space of the first image, and mapping the pixel locations of each of the first and at least one second images to a pixel coordinate space representative of the medication tray, and when the updated determined number equals or exceeds the threshold number apply the edge detection algorithm to the combined first and at least one second images to identify the boundary outline of the medication tray based upon the plurality of boundary markers, and generate the current medication stocking list of the medication tray based upon the identified boundary outline and the tray identifier from the first and at least one second images.

19. The method of claim 18 wherein using the mobile wireless communications device comprises using the mobile wireless communication device to, when the determined number does not exceed the threshold number, determine whether the at least one second image is a same image of the first image based upon pixel distances, and when so, discard the at least one second image.

20. The method of claim 19 wherein the first and at least one second images each comprise respective first and at least one second pixel sets; and wherein using the mobile wireless communications device comprises using the mobile wireless communication device to determine whether the at least one second image is the same as the first image based upon alignment of the first and at least one second pixel sets.

21. The method of claim 18 wherein using the mobile wireless communications device comprises using the mobile wireless communications device to:
- extract red, green, blue (RGB) pixel data from the at least one image;
- convert the RGB pixel data to hue saturation value (HSV) space;
- segment the at least one image into colored segments based upon the HSV space; and
- apply the edge detection algorithm to the colored segments to identify the boundary outline of the medication tray.

22. The method of claim 18 wherein using the mobile wireless communications device comprises using the mobile wireless communications device to apply contour tracing to identify the boundary outline of the medication tray.

23. A non-transitory computer readable medium for a medication inventory system comprising a medication tray comprising a plurality of compartments for storing respective medications, the medication tray comprising a boundary wall defining a boundary outline of the medication tray, and the medication tray having a tray identifier associated therewith for identifying a desired medication stocking list of desired medications within the medication tray, the non-transitory computer readable medium comprising computer executable instructions that when executed by a controller of a mobile wireless communications device cause the controller to perform operations comprising:
- obtaining a first image of the medication tray; and
- determining a number of a plurality of boundary markers carried by the boundary wall of the medication tray from the first image, and when the determined number equals or exceeds a threshold number
  - applying an edge detection algorithm to the first image to identify the boundary outline of the medication tray based upon a plurality of boundary markers, and
  - generating a current medication stocking list of the medication tray based upon the identified boundary outline and the tray identifier from the first image; and
- when the determined number does not exceed the threshold number,
  - obtaining at least one second image of the medication tray,
  - determining an updated number of the plurality of boundary markers from the first and at least one second image by combining the first and at least one second images based upon determining image pixel locations in each of the first and at least one second images, mapping the pixel locations of the at least one second image to a pixel coordinate space of the first image, and mapping the pixel locations of each of the first and at least one second images to a pixel coordinate space representative of the medication tray, and when the updated determined number equals or exceeds the threshold number
    - applying the edge detection algorithm to the combined first and at least one second images to identify the boundary outline of the medication tray based upon the plurality of boundary markers, and
    - generating the current medication stocking list of the medication tray based upon the identified boundary outline and the tray identifier from the first and at least one second images.

24. The non-transitory computer readable medium of claim 23 wherein the operations comprise, when the determined number does not exceed the threshold number, determining whether the at least one second image is a same image of the first image based upon pixel distances, and when so, discard the at least one second image.

25. The non-transitory computer readable medium of claim 24 wherein the first and at least one second images each comprise respective first and at least one second pixel sets; and wherein the operations comprise determining whether the at least one second image is the same as the first image based upon alignment of the first and at least one second pixel sets.

26. The non-transitory computer readable medium of claim 23 wherein the operations comprise:
- extracting red, green, blue (RGB) pixel data from the at least one image;
- converting the RGB pixel data to hue saturation value (HSV) space;
- segmenting the at least one image into colored segments based upon the HSV space; and
- applying the edge detection algorithm to the colored segments to identify the boundary outline of the medication tray.

* * * * *